(12) United States Patent
Saiko et al.

(10) Patent No.: US 11,266,345 B2
(45) Date of Patent: Mar. 8, 2022

(54) APPARATUS FOR VISUALIZATION OF TISSUE

(71) Applicant: Swift Medical Inc., Toronto (CA)

(72) Inventors: Guennadi Saiko, Mississauga (CA); Kenneth Macko, Toronto (CA); Andrei Betlen, Pickering (CA)

(73) Assignee: Swift Medical Inc., Toronto (CA)

( * ) Notice: Subject to any disclaimer, the term of this patent is extended or adjusted under 35 U.S.C. 154(b) by 0 days.

(21) Appl. No.: 17/260,664

(22) PCT Filed: Jul. 16, 2019

(86) PCT No.: PCT/CA2019/050981
§ 371 (c)(1),
(2) Date: Jan. 15, 2021

(87) PCT Pub. No.: WO2020/014779
PCT Pub. Date: Jan. 23, 2020

(65) Prior Publication Data
US 2021/0259625 A1     Aug. 26, 2021

Related U.S. Application Data

(60) Provisional application No. 62/698,799, filed on Jul. 16, 2018.

(51) Int. Cl.
*A61B 5/00* (2006.01)

(52) U.S. Cl.
CPC ............ *A61B 5/445* (2013.01); *A61B 5/0013* (2013.01); *A61B 5/0077* (2013.01); *A61B 5/6898* (2013.01); *A61B 5/742* (2013.01)

(58) Field of Classification Search
CPC ....... A61B 5/445; A61B 5/742; A61B 5/6898; A61B 5/0013; A61B 5/0077;
(Continued)

(56) References Cited

U.S. PATENT DOCUMENTS 5,074,306 A * 12/1991 Green .................... A61B 5/445
600/317
6,251,070 B1 * 6/2001 Khazaka .............. A61B 5/0059
600/306

(Continued)

FOREIGN PATENT DOCUMENTS

WO    WO-2017/012675 A1    1/2017
WO    WO-2017/155265 A1    9/2017

OTHER PUBLICATIONS

International Searching Authority, International Search Report and Written Opinion for International Application No. PCT/CA2019/050981; dated Oct. 9, 2019, (6 pages), Canadian Intellectual Property Office, Quebec, Canada.

*Primary Examiner* — May A Abouelela
(74) *Attorney, Agent, or Firm* — Alston & Bird LLP

(57) ABSTRACT

A tissue imaging system comprising a computing device, tissue visualization application, image capturing unit, and an illumination unit, is configured to capture measurement data. The visualization application extracts visualizations of tissue health indicators from the measurement data. The application generates an interface with one or more interface elements corresponding to the visualization of tissue health indicators.

20 Claims, 10 Drawing Sheets

(58) Field of Classification Search
CPC . A61B 5/7264; A61B 5/14551; A61B 5/1455; A61B 5/14546; A61B 5/4878; A61B 5/4875; A61B 5/0075; G03B 33/08; G03B 2215/0514; G03B 15/05
USPC ............................................. 600/306
See application file for complete search history.

(56) References Cited

U.S. PATENT DOCUMENTS

| | | | | |
|---|---|---|---|---|
| 6,571,003 | B1* | 5/2003 | Hillebrand | A61B 5/0064 382/100 |
| 6,685,635 | B2* | 2/2004 | Shani | A61B 5/0059 356/425 |
| 6,792,137 | B2* | 9/2004 | Kenet | G16H 10/20 382/128 |
| 7,179,227 | B2* | 2/2007 | Shirai | A61B 5/0059 600/306 |
| 7,454,046 | B2* | 11/2008 | Chhibber | A61B 5/442 382/118 |
| 7,657,101 | B2* | 2/2010 | Christiansen, II | G06T 7/90 382/218 |
| 8,026,942 | B2* | 9/2011 | Payonk | H04N 5/2354 348/77 |
| 8,116,852 | B2* | 2/2012 | Baker, Jr. | A61B 5/0059 600/476 |
| 8,591,413 | B2* | 11/2013 | Kruglick | A61B 5/441 600/306 |
| 9,662,076 | B2* | 5/2017 | Jia | A61B 6/08 |
| 10,127,661 | B2* | 11/2018 | Wang | A61B 5/0066 |
| 10,182,757 | B2* | 1/2019 | Gareau | A61B 5/0075 |
| 2004/0125996 | A1* | 7/2004 | Eddowes | A61B 5/442 382/128 |
| 2004/0202685 | A1* | 10/2004 | Manzo | A45D 44/00 424/401 |
| 2004/0218810 | A1* | 11/2004 | Momma | A61B 5/0064 382/162 |
| 2007/0002479 | A1* | 1/2007 | Menke | A61B 5/0079 359/892 |
| 2007/0064979 | A1* | 3/2007 | Chhibber | G06K 9/2018 382/118 |
| 2008/0161661 | A1* | 7/2008 | Gizewski | A61B 5/0059 600/306 |
| 2008/0194928 | A1* | 8/2008 | Bandic | A61B 5/442 600/306 |
| 2008/0214907 | A1* | 9/2008 | Gutkowicz-Krusin | A61B 5/0059 600/306 |
| 2008/0319283 | A1* | 12/2008 | Cotton | A61B 5/0059 600/306 |
| 2009/0080727 | A1* | 3/2009 | Cotton | G06T 7/42 382/128 |
| 2009/0177051 | A1* | 7/2009 | Arons | A61B 5/445 600/306 |
| 2009/0220415 | A1* | 9/2009 | Shachaf | A61K 49/0004 424/1.11 |
| 2010/0185064 | A1* | 7/2010 | Bandic | A61B 5/415 600/306 |
| 2010/0271470 | A1* | 10/2010 | Stephan | A61B 5/445 348/77 |
| 2011/0117025 | A1* | 5/2011 | Dacosta | G01N 21/6456 424/9.6 |
| 2011/0288385 | A1* | 11/2011 | Stamatas | A61B 5/0059 600/306 |
| 2011/0301441 | A1* | 12/2011 | Bandic | A61B 5/0059 600/306 |
| 2012/0041283 | A1* | 2/2012 | Krishnan | A61B 5/448 600/306 |
| 2012/0041284 | A1* | 2/2012 | Krishnan | A61B 5/448 600/306 |
| 2012/0172685 | A1* | 7/2012 | Gilbert | A61B 5/411 600/306 |
| 2013/0094730 | A1* | 4/2013 | Segman | A61B 5/445 382/128 |
| 2013/0096392 | A1* | 4/2013 | Adams | A61B 5/0064 600/301 |
| 2013/0204101 | A1* | 8/2013 | Rumberg | A61B 5/0062 600/306 |
| 2014/0088380 | A1* | 3/2014 | Sprigle | A61B 5/0077 600/306 |
| 2014/0378779 | A1* | 12/2014 | Freeman | A61B 5/1032 600/301 |
| 2015/0099947 | A1* | 4/2015 | Qu | A61B 5/442 600/306 |
| 2015/0105635 | A1* | 4/2015 | Yoshida | A61B 8/0858 600/306 |
| 2015/0297130 | A1* | 10/2015 | Stamnes | G06T 7/44 600/306 |
| 2015/0374277 | A1* | 12/2015 | Patwardhan | A61B 5/0013 600/306 |
| 2016/0135730 | A1* | 5/2016 | Arai | A61B 5/742 600/306 |
| 2018/0333053 | A1* | 11/2018 | Verkruijsse | A61B 5/0077 |
| 2018/0333589 | A1* | 11/2018 | Kim | A61B 5/444 |
| 2019/0069836 | A1* | 3/2019 | Hettrick | A61B 5/447 |
| 2019/0082998 | A1* | 3/2019 | Nowroozi | A61B 5/445 |
| 2019/0090751 | A1 | 3/2019 | Hwang et al. | |
| 2019/0125197 | A1* | 5/2019 | Fukuda | G06T 7/0016 |
| 2019/0216340 | A1* | 7/2019 | Holz | A61B 5/7221 |
| 2019/0231249 | A1* | 8/2019 | Dascalu | A61B 5/0095 |
| 2019/0388022 | A1* | 12/2019 | Talgorn | A61B 5/02055 |
| 2020/0003683 | A1* | 1/2020 | Haddad | A61B 5/445 |
| 2020/0046999 | A1* | 2/2020 | Lim | A61B 5/0077 |
| 2020/0092534 | A1* | 3/2020 | Eckhouse | A61B 5/443 |
| 2020/0113438 | A1* | 4/2020 | Bourquin | A61B 18/203 |
| 2020/0113441 | A1* | 4/2020 | Varghese | A61B 5/7278 |
| 2020/0121243 | A1* | 4/2020 | Anderson | A61B 5/00 |
| 2020/0121262 | A1* | 4/2020 | De Haan | A61B 5/0245 |
| 2020/0129069 | A1* | 4/2020 | Inglese | A61B 5/1077 |
| 2020/0176099 | A1* | 6/2020 | Welss | A61B 5/443 |
| 2020/0179713 | A1* | 6/2020 | Subhash | A61N 5/0616 |
| 2020/0281512 | A1* | 9/2020 | Grubb | A61B 5/489 |
| 2020/0281513 | A1* | 9/2020 | Grubb | A61B 5/489 |
| 2020/0320683 | A1* | 10/2020 | Horiuchi | A61B 5/444 |
| 2020/0383630 | A1* | 12/2020 | Xu | A61B 5/0075 |
| 2021/0052212 | A1* | 2/2021 | Yaroslavsky | A61B 5/4836 |

\* cited by examiner

APPARATUS FOR VISUALIZATION OF TISSUE

CROSS REFERENCE TO RELATED APPLICATIONS

This application is a National Stage Application, filed under 35 U.S.C. § 371, of International Application No. PCT/CA2019/050981, filed Jul. 16, 2019, which claims priority to U.S. Provisional Application No. 62/698,799, filed Jul. 16, 2018; the contents of both of which as are hereby incorporated by reference in their entireties.

BACKGROUND

Related Field

The improvements generally relate to the field of medical devices.

Description of Related Art

People suffer from chronic and compromised wounds with debilitating pain and reduced quality of life for those whose health is already compromised. Patients with this condition often present to a doctor at late stages of the disease, which leads to many amputations, which may be avoidable. Moreover, proper diagnostics requires specialized vascular labs, which precludes these types of tests from being performed outside major hospitals and in an expedited fashion.

The wound is considered chronic if it is not healed within four weeks. The tissue health and wound healing process can be compromised by various factors, including insufficient blood supply, edema, and the presence of bacteria. These factors (oxygenation/perfusion, subepidermal moisture, and bacteria presence) among others will be referred to as tissue health indicators.

Multispectral (hyperspectral) imaging is a promising non-invasive optical modality for early detection of problematic wounds.

Visualization of skin distribution of oxyhemoglobin and deoxyhemoglobin can give insight into perfusion and oxygenation of the tissue. It can be used for assessment of tissue health (for example, ischemia).

Such as elevated levels of subepidermal moisture are typical for pressure injuries, visualization of water distribution in tissue can be used for early (pre-ulcer) diagnostics of pressure injuries.

Fluorescence imaging is a promising non-invasive optical modality for detection of bacterial burden. Visualization of bacterial burden can be used to assess bacterial burden and guide swabbing and cleansing.

BRIEF SUMMARY

In accordance with an aspect, there is provided a process for generating visualizations of tissue. The process captures measurement data by a user device (e.g., smartphone), and processes the measurement data using the visualization application. The process extracts indications of tissue health from the processed measurement data, and stores or transmits the underlying data. The process generates interface elements corresponding to the visualization tissue health indicators.

In some embodiments, the process involves calibrating the visualization application using a reference object.

In some embodiments, a small self-reference can be used to position the device properly.

In some embodiments, a small self-reference can be used to calibrate the measurement data based on an intensity of illumination.

In some embodiments, an illumination unit independent of the mobile device can be used for calibration and capture measurements together with a camera, laptop, or tablet.

In accordance with an aspect, there is provided a tissue imaging system comprised of a user device with a visualization application, an image capturing unit, and an illumination unit. The illumination unit is configured to illuminate the target area; the image capturing unit captures measurement data, the visualization application extracts visualizations of tissue health indicators from the measurement data and generates an interface with one or more interface elements corresponding to the visualization of tissue health indicators.

In accordance with an aspect, there is provided a tissue visualization system connected to a tissue imaging system (user device with a visualization application, an image capturing unit, and an illumination unit). The illumination unit illuminates the target area; the image capturing unit captures measurement data. The visualization application extracts visualization of tissue health indicators from the measurement data and transmits the visualization of tissue health indicators or underlying data to the tissue visualization system. The tissue visualization system processes and stores the visualization of tissue health indicators or underlying data, and displays them on user devices.

In accordance with an aspect, there is provided a portable illumination apparatus for facilitating visualizations of tissue. The apparatus comprises: a portable housing for detachable attachment proximal to an image capturing unit; and an illumination unit comprising one or more narrow band light sources configured to shine m flashes at n predetermined wavelengths, wherein $n/4 \leq m \leq n$.

In accordance with a further aspect, the illumination unit further comprises a lens covering the one or more light sources, and having a focal length that is 80%-120% of a working distance between the illumination unit and a target area of tissue.

In yet a further aspect, the one or more light sources is configured to provide flashes that are at least one of: (i) $405 \pm 10$ nm wavelength, and having at least one of (a) a long pass filter with a cut-on wavelength of $450 \pm 25$ nm or (b) a bandpass filter with transmission in a 425 nm-1000 nm range; (ii) two wavelengths in a 450 nm-750 nm range, at least one of which in the green range; (iii) three wavelengths in a 450 nm-750 nm range, at least one of which in the green range; or (iv) $970 \pm 10$ nm wavelength.

In accordance with a further aspect, the illumination unit further comprises at least one of (i) a controller to control illumination of the one or more light sources, and (ii) a rechargeable battery for powering the apparatus.

In accordance with another aspect, the one or more light sources are arranged along a central aperture having a radius of 0.5-3 cm.

In accordance with a further aspect, the one or more light sources are arranged in a ring having a radius of 1.5-6 cm.

In accordance with an aspect, the portable housing comprises a compression clip for mounting the apparatus on a mobile device along at least one edge of the mobile device and proximal to a camera of the mobile device.

In accordance with another aspect, the portable housing comprises a spring clip for mounting the apparatus on a mobile device along at least one edge of the mobile device and proximal to a camera of the mobile device.

In accordance with a further aspect, there is provided a tissue imaging system for visualization of tissue health indicators comprising a portable computing device, an image capture unit, and an illumination unit. The illumination unit comprises one or more narrow band light sources configured to shine m flashes at n predetermined wavelengths, wherein n/4≤m≤n. The image capture unit and the illumination unit are configured to capture measurement data for a target area of tissue. The computing device comprises a processor configured to access and execute instructions in accordance with a tissue visualization application stored in a non-transitory computer-readable memory of the computing device, for capturing measurement data, and pre-processing and processing the measurement data to generate tissue health indicators.

In accordance with an aspect, the computing device comprises a mobile device and the image capture unit is a camera integrated with the mobile device.

In accordance with a further aspect, the illumination unit of the tissue imaging system comprises any of the embodiments of the illumination apparatus described above.

In accordance with yet a further aspect, the portable illumination unit further comprises a wireless communication module for receiving commands from the computing device.

In accordance with a further aspect, there is provided a tissue visualization system operatively connected to one or more tissue imaging systems (such as any of the tissue imaging systems described above), comprising a communications module for communicating with the one or more tissue imaging systems, a system processor, and system non-transitory computer-readable memory thereon, configured to receive measurement data and tissue health indicators from the one or more tissue imaging systems and to generate a visualization of tissue health indicators of tissue images received from the one or more tissue imaging systems, for display to a user display unit.

In accordance with a further aspect, there is provided a method for generating visualizations of tissue. The method comprises: positioning a computing device at a proper distance from a target area of the tissue for capturing an image of the target area, the computing device comprising a processor and a non-transitory computer-readable memory storing computer-executable instructions comprising a tissue visualization application; capturing measurement data using an image capturing unit and an illumination unit, the image capturing unit and the illumination unit communicatively coupled to the computing device and the illumination unit configured to shine m flashes at n predetermined wavelengths during capturing of the measurement data, wherein n/4≤m≤n; pre-processing the measurement data using the tissue visualization application to obtain normalized images; extracting indications of tissue health indicators from the pre-processed measurement data; generating interface elements corresponding to the visualization tissue health indicators; and storing and/or transmitting the indications of the tissue health indicators.

In accordance with an aspect, the method further comprises, prior to capturing the measurement data: capturing a reference image, wherein the positioning the computing device for the reference image capturing comprises positioning the computing device using a reference object.

In accordance with a further aspect, the illumination unit and the computing device are configured to provide a working distance of 15±5 cm from the target area of tissue.

In accordance with yet a further aspect, the positioning of the computing device for capturing the measurement data comprises positioning the computing device using a self-reference object.

In accordance with another aspect, pre-processing comprises at least one of (i) registering images to avoid camera motion artifacts, (ii) subtracting images with no illumination from the illumination unit from images with illumination from the illumination unit to account for the presence of ambient light, (iii) recalibrating each measurement accordingly to control parameters related to intensity of illumination using a self-reference object positioned within the target area, (iv) dividing the intensity images on reference images to obtain normalized images, and/or (v) flattening the obtained images to account for reflections from curved surfaces.

In accordance with an aspect, camera exposure time is T and a flash time is T or any whole number multiple of T.

In accordance with another aspect, the camera exposure time is 50 ms.

In accordance with a further aspect, the measurement data comprises wound-related data.

Many further features and combinations thereof concerning embodiments described herein will appear to those skilled in the art following a reading of the instant disclosure.

BRIEF DESCRIPTION OF THE FIGURES

Embodiments will now be described, by way of example only, with reference to the attached figures, wherein in the figures.

DETAILED DESCRIPTION OF VARIOUS EMBODIMENTS

Figure 1:
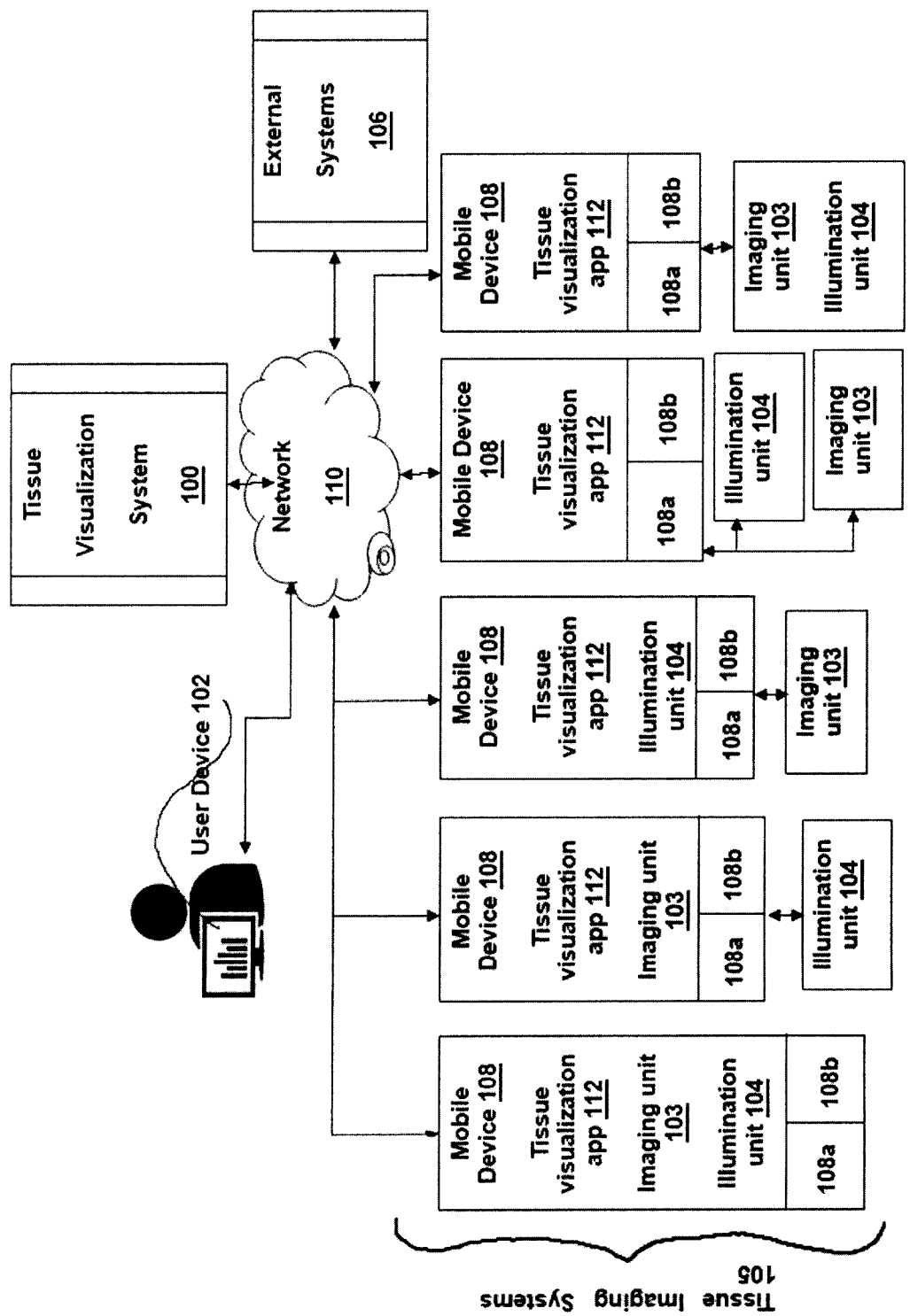
FIG. 1 depicts a view of an example of the overall system architecture with various configurations of tissue imaging systems according to some embodiments.

Some clinical-grade tools can only be used in specialized medical establishments. They can be large, require special training, and are mostly suitable for the use in inpatient settings only. For example, they cannot be easily carried to a patient's home or remote communities. Thus, these solutions cannot be used as early diagnostic tools as a patient would have to be referred to a hospital having one of these tools.

Many people suffer from diabetes. Diabetic foot ulcers (DFU) and the resulting lower extremity amputations are a frequent, disabling and costly complication of diabetes. Many diabetics can develop a foot ulcer. DFU is a cause of non-traumatic below knee amputation. In addition to the reduced quality of life, amputees might not survive for that long after amputation. Consequently, early detection of DFU can lead to better outcomes, thus saving limbs and lives.

Peripheral vascular disease (PVD) affects arteries (peripheral arterial disease, PAD) and veins (chronic venous insufficiency, CVI). PAD is of particular importance, as it affects about eight million Americans and is responsible for 10% of all leg ulcers.

Pressure ulcers (PU) or pressure injuries represent a serious health problem to patients impacting up to 25-50% of patients across acute and long-term care settings.

The cost of treatment of diabetic foot ulcer, pressure ulcer, and leg ulcer is high. Diagnosing these conditions at an earlier stage (e.g., before actual ulceration) might result in significant financial savings for healthcare systems and patients.

Other clinical indications associated with abnormal blood perfusion and/or oxygenation, such as skin cancer (angiogenesis), port-wine stains, and skin disorders, can benefit from a system for tissue imaging.

Subepidermal moisture, a measure of localized edema, is associated with erythema, Stage I and II PUs [Bates-Jensen 2007, Bates-Jensen 2008, Guihan 2012, Ching 2011], and can (ii) differentiate between healthy skin and skin with pressure-induced tissue damage [Harrow 2014] and (iii) serve as a predictor of imminent ulceration (PUs, sDTIs) in various populations [Bates-Jensen 2007, Bates-Jensen 2008, Bates-Jensen 2009]. Thus, changes in measures of subepidermal moisture could be utilized for both prevention and detection of PUs. Radiofrequency impedance measurement with spatially separated electrodes is a current standard way to measure skin moisture including subepidermal moisture. However, it is a contact single-point measurement technique, which may suffer from operator inconsistency.

Near-Infrared spectroscopy (NIR) reflectance can be used to determine water content in the skin. Water spectrum dominating NIR spectra with overtone bands of the O—H bonds with peak absorption at 760 nm, 970 nm (due to the second overtone of the O—H stretching band), 1190 nm (the combination of the first overtone of the O—H stretching and the O—H bending band), 1450 nm (first overtone of the OH-stretching band and a combination band), and 1940 nm (combination of the O—H stretching band and the O—H bending band). [Luck 1974].

Water absorption at 1440 nm is 30 times stronger than at 1190 nm, which in turn is more than two times stronger than absorption at 970 nm. Thus, 1440 nm and 1920 nm wavelengths are suitable for imaging of water content in uppermost skin layers (stratum corneum), while 970 nm and 1190 nm can be used for water content determination and imaging in deeper skin layers, including epidermis, dermis (1190 nm) and even subcutaneous tissues (970 nm).

Bacteria presence can significantly impact tissue health and wound healing progress. Bacteria are always present in the wound. There are several distinct levels of bacterial burden in the wound: contamination, colonization, and infection.

Wound contamination is the presence of non-replicating organisms in the wound. All chronic wounds are contaminated. These contaminants come from the indigenous microflora and/or the environment.

Wound colonization is the presence of replicating microorganisms adherent to the wound in the absence of injury to the host. Most of these organisms are normal skin flora; such as *Staphylococcus epidermidis*, another coagulase negative Staph., *Corynebacterium* sp., *Brevibacterium* sp., *Proprionibacterium acnes*, and *Pityrosporum* sp.

Wound Infection is the presence of replicating microorganisms within a wound that cause host injury. Primarily, pathogens are of concern here, such as *Staphylococcus aureus*, Beta-hemolytic *Streptococcus* (*S. pyogenes, S. agalactiae*), *E. coli, Proteus, Klebsiella*, anaerobes, *Pseudomonas, Acinetobacter*, and *Stenotrophomonas* (*Xanthomonas*).

Contamination and colonization by low concentrations of microbes are considered normal and are not believed to inhibit healing. However, critical colonization and infection are associated with a significant delay in wound healing.

Clinical testing for bacterial presence includes analysis of swabs from the tissue. In addition to long processing time (several days), these tests suffer from possible contamination during swabbing and randomness in the selection of swabbing sites. Thus, current clinical diagnostics techniques are sub-optimal.

Portable fluorescence imaging can be used for visualization of bacterial presence. It was found that while excited at 405 nm, *S. aureus, S. epidermidis, Candida, S. marcescens, Viridans streptococci, Corynebacterium diphtheriae, S. pyogenes, Enterobacter*, and *Enterococcus* produced red (610-640 nm) fluorescence from porphyrin [Kjeldstad 1985] while *P. aeruginosa* produced a bluish-green (450-520 nm) fluorescence from pyoverdin [Cody 1987]. Thus, fluorescence imaging can be used to assess bacterial burden and guide swabbing and wound cleansing.

Thus, multispectral/hyperspectral-based reflectance imaging, fluorescence imaging or their combination can provide valuable insights on tissue health and wound healing potential.

Embodiments described herein can provide a tool for tissue imaging.

FIG. 1 depicts a view of an example tissue visualization system 100 that connects to tissue imaging systems 105 via network 110.

Tissue imaging system 105 is a device for visualization of abnormalities of blood circulation, moisture distribution, and bacterial burden in surface tissues (skin or mucosa). For example, the device can be used for identification of ischemic or angiogenic conditions. It can be used by primary care physicians, nurses, or even patients themselves in any type of settings: inpatient, outpatient, long-term facilities, patient's home, and so on, thus allowing earlier identification of problematic wounds. Tissue imaging system 105 may comprise a computing device 108 which may comprise a mobile device 108, processor(s) 108a, non-transitory computer readable storage medium or memory 108b, image capturing unit 103, and illumination unit 104. Memory 108b may comprise computer executable instructions comprising tissue visualization app 112.

Computing device 108 may be an off-the-shell computing device (for example, a mobile device, smartphone, tablet, laptop, a personal computer) or a custom-built computing device. In an example embodiment, computing device 108 comprises a smartphone.

Tissue visualization app 112 coordinates image capturing unit 103 and illumination unit 104 during data capturing, process images, display results on computing device 108, and store and/or transmit data to tissue visualization system 100.

Image capturing unit 103 may comprise an internal (built-in to computing device 108) or external device capable of capturing images. In an example embodiment, image capturing unit 103 comprises a 3 channel (RGB) or 4 channel (RGB-NIR) camera.

Illumination unit 104 may comprise an internal (built-in to computing device 108) or external device (e.g., multi-spectral flash) capable of illuminating a target area with required intensity, wavelengths, and duration.

Example tissue imaging system 105 architectures are presented on FIG. 1. In some embodiments, the tissue imaging system 105 can be a single device. In some embodiments, the tissue imaging system 105 can have two separate parts (e.g., image capturing unit 103 built-in to computing device 108 and a separate illumination unit 104, or illumination unit 104 built-in to computing device 108 (e.g., a mobile device 108) and a separate image capturing unit 103). In some embodiments, tissue imaging system 105 can have three separate parts (for example, a computing device 108, a separate image capturing unit 103, and a separate illumination unit 104). The separate components of tissue imaging system 105 may communicate by known wired or wireless communications protocols.

In an example embodiment, illumination unit 104 can be a device attached (e.g., clip-on or by compression clip) to a computing device 108, such as a mobile device or smartphone.

In some embodiments, illumination unit 104 can be connected or synchronized with the tissue visualization application 112 (installed on or otherwise accessible by computing device 108) for example by known wireless connections (for example, Bluetooth™), optic or optoelectric coupling, or wired connection. In some embodiments, the illumination unit 104 can be triggered manually, and the visualization application 112 recognizes the light sequence and synchronizes image capturing.

In some embodiments, the image capturing unit 103 can connect to the tissue visualization application 112 (installed on or otherwise accessible by computing device 108 (e.g., a mobile device 108)) for example by known wireless connections (for example, Bluetooth™), optic or optoelectric coupling, or wired connection.

The tissue visualization application 112 can, in turn, be connected to tissue visualization system 100 (which may comprise, e.g., a backend server). The tissue visualization system 100 can collect data from tissue visualization applications 112 of tissue imaging systems 105, via network 110. The tissue visualization system 100 can transmit the data (or transformations and aggregations of the data) to user device 102, which may comprise any device with computer processing capability (e.g., computer, laptop, tablet, or smartphone) for use by a user (e.g. a physician or other user). Thus, a qualified specialist may review the data collected by tissue visualization system 100 from one or more tissue imaging systems 105 used to capture image(s) in a different location by, e.g., a frontline health practitioner (e.g., nurse) or patient. This may facilitate early diagnostic by the physician.

Tissue imaging system 105 can capture measurement data as images of a patient's tissue. The visualization application 112 can extract visualizations of tissue health indicators from the measurement data. The visualization application 112 can generate one or more interface elements corresponding to the visualization of tissue health indicators. The interface elements populate an interface for display on the computing device 108 (e.g., a mobile device 108).

In some embodiments, the computing device 108 can connect to a tissue visualization system 100 to transmit the measurement data and the visualization of tissue health indicators, for example. The tissue visualization system 100 can aggregate the measurement data and the visualization of tissue health indicators from multiple tissue imaging systems 105. The tissue visualization system 100 can process and store the measurement data and the visualization of tissue health indicators.

In some embodiments, tissue imaging system 105 can connect to a user device 102. In some embodiments, the computing device 108 (e.g., a mobile device 108) with tissue visualization app 112 can receive and aggregate measurement data from multiple tissue imaging system(s) 105, and generate the visualization of tissue health indicators for transmission to tissue visualization system 100. The tissue visualization system 100 can aggregate the measurement data and the visualization of tissue health indicators from multiple tissue imaging systems 105.

The tissue visualization system 100 receives imaging data from the tissue imaging system(s) 105 to generate a visualization of tissue and detect wounds and abnormalities. The tissue visualization system 100 and tissue imaging system(s) 105 connect to other components in various ways including directly coupled, and indirectly coupled via network 110. Network 110 (which may comprise multiple communications networks) is capable of carrying data and can involve wired connections, wireless connections, or a combination thereof. Network 110 may involve different network communication technologies, standards, and protocols.

Figure 2:
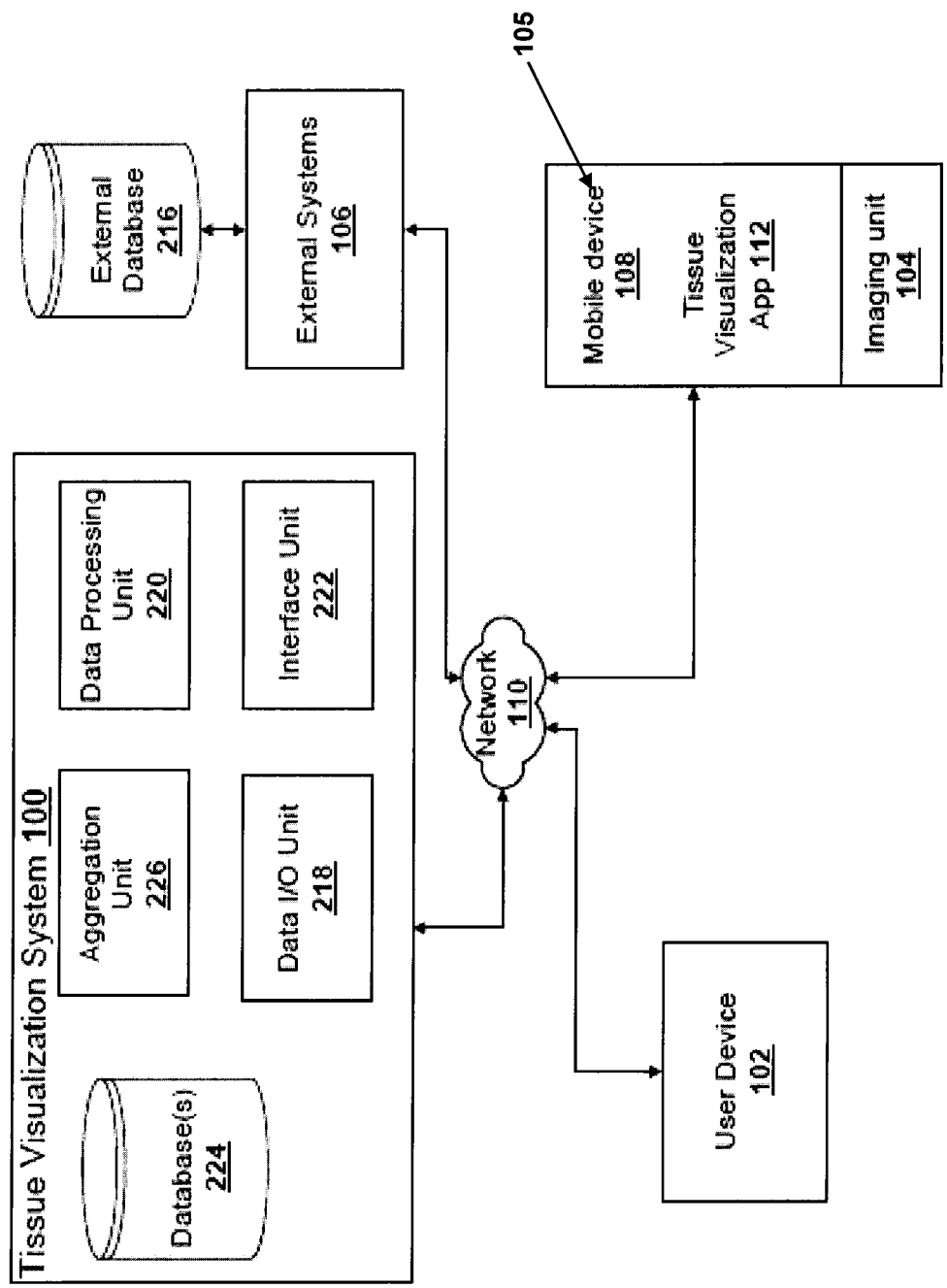
FIG. 2 depicts a view of an example of a tissue visualization system according to some embodiments.

FIG. 2 depicts a view of an example tissue visualization system 100 according to some embodiments, interfaced with system components.

Tissue visualization system 100 receives imaging data from the tissue imaging system 105 via data I/O unit 218. Data I/O unit 218 facilitates transmission of data to data processing unit 220. Data processing unit 220 processes data received from the data I/O unit 218 or one or more databases 224. For example, data processing unit 220 can apply one or more algorithms or extract data that may be used for, or that may facilitate the visualization or processing related to detection of problematic wounds or abnormalities of blood circulation, for example, in surface tissues. Data processing unit 220 can extract, create, and/or aggregate from that data a wound size and/or a map, visualization, or indication of oxygenation, oxyhemoglobin, deoxyhemoglobin, perfusion, water, bacteria presence, and/or other indicia that may suggest abnormalities of tissue health, for example, in surface tissues.

Data processing unit 220 can receive, via data I/O unit 218 and network 110, instructions for computation from one or more external systems 106, user device 102, tissue imaging system 105, and/or tissue visualization app 112. The instructions for computation can be used by data processing unit 220 to facilitate the extraction, creation, and/or aggregation of data providing a wound size and/or a map, visualization, or indication of oxygenation, oxyhemoglobin, deoxyhemoglobin, perfusion, water, bacterial presence and/or other indicia that may suggest abnormalities of tissue health, for example, in surface tissues. In some embodiments, data processing unit 220 can process imaging data to prepare the data for presentation via the interface unit 222 in an appropriate form or to prepare the data for transmission to an external system 106, user device 102, and/or tissue imaging system 105 to be presented in an appropriate form.

Data processing unit 220 can receive data or processed data from aggregation unit 226 and may extract, create, and/or aggregate from that data, data providing a wound size and/or a map, visualization, or indication of oxygenation, oxyhemoglobin, deoxyhemoglobin, perfusion, water, bacterial presence and/or other indicia that may suggest abnormalities of tissue health, for example, in surface tissues. The map, visualization, or other indication that can be extracted, created, and/or aggregated by data processing unit 220 can reflect imaging data or measurements corresponding to a plurality of patients. The data processed by data processing unit 220 may be imaging data collected at one or more tissue imaging systems 105 and/or one or more user devices 102. The data processed by data processing unit 220 may be measurement data reflecting one or more images of a patient's tissue.

Aggregation unit 226 can receive via data I/O unit 218 and/or one or more databases 224 imaging data corresponding to a plurality of patients, tissue imaging systems 105, or user devices 102. Aggregation unit 226 can aggregate or modify the data by applying instructions for computation, and so may comprise one or more processors. Aggregation unit 226 can cause the aggregated or modified data to be transmitted to data processing unit 220 where the data can be processed to prepare the data for presentation via interface unit 222 in an appropriate form or to prepare the data for transmission to an external system 106, user device 102, and/or tissue imaging system 105 to be presented in an appropriate form.

Aggregation unit 226 can receive processed data from data processing unit 220 corresponding to a plurality of patients, tissue imaging systems 105, or user devices 102. Aggregation unit 226 can aggregate or modify the processed data by applying the instructions for computation. Aggregation unit 226 can cause the aggregated or modified data to be transmitted to data processing unit 220 where the data can be further processed to prepare the data for presentation via interface unit 222 in an appropriate form or to prepare the data for transmission to an external system 106, user device 102, and/or tissue imaging system 105 to be presented in an appropriate form.

Aggregation unit 226 can receive via data I/O unit 218 and instructions for computation from one or more external systems 106, user device 102, tissue imaging system 105, and/or tissue visualization app 112. The instructions for computation can be used by aggregation unit 226 to facilitate aggregation of imaging corresponding to a plurality of patients.

Tissue visualization system 100 can receive imaging data, for example, aggregate imaging data, from computing device 108 (e.g., a mobile device 108) via data I/O unit 218. Tissue visualization system 100 can receive imaging data, for example, aggregate imaging data, from external systems 106 via data I/O unit 218. Tissue visualization system 100 can receive computer instructions for processing or computation from external systems 106. External systems 106 can store, cause to be stored, and/or receive data from one or more external databases 216.

Aggregation unit 226 can receive via data I/O unit 218 and network 110 the instructions for computation from one or more external systems 106, user device 102, tissue imaging system 105, and/or tissue visualization application 112.

Tissue visualization system 100 can be associated with one or more databases or data storages 224, for example, one or more local databases. The one or more databases 224 can store or process data received or transmitted by data I/O unit 218, data processing unit 220, and/or aggregation unit 226. The data stored in the one or more databases 224 can be accessed by various units, including data I/O unit 218, data processing unit 220, and/or aggregation unit 226. For example, data I/O unit 218 may cause database 224 to store data received via network 110 and/or from user device 102, external systems 106, tissue imaging system 105, and/or tissue visualization app 112. Data processing unit 220 and aggregation unit 226 can cause data to be retrieved from database 224, for example, before processing or aggregating the data.

Data processing unit 220 can cause data to be stored in database or data storage 224 after it processes the data by applying instructions or extracting data that may be used for or facilitate the visualization or processing related to detection of problematic wounds or abnormalities of blood circulation in surface tissues. Data processing unit 220 can retrieve the processed data from database or data storage 224 and cause the processed data to be transmitted to the interface unit 222 or network 110, for example, for presentation to a patient or physician using user device 102, 105 or 106, for example.

Data processing unit 220 may cause data to be stored in database or data storage 224 after it extracts, creates, and/or aggregates data providing a wound size and/or a map, visualization, or indication of oxygenation, oxyhemoglobin, deoxyhemoglobin, perfusion, water, bacterial presence and/or other indicia that may suggest abnormalities of tissue health, for example, in surface tissues.

Data processing unit 220 may use Machine Learning (including supervised ML and unsupervised ML) to extract information from collected images and other data. In particular, data processing unit 220 can build and train models, which can discriminate between various conditions and provide users with additional information. In some embodiments, data processing unit 220 uses convolutional neural networks for automatic or semi-automatic detection and/or classification of the skin or wound conditions. In some embodiments, ML models built and trained using other tools may be deployed to data processing unit 220 for image/data detection/classification, such as from an external system 106.

Aggregation unit 226 can cause data to be stored in database 224 after it aggregates imaging data or processed data that corresponds to a plurality of patients and/or user devices 102. Aggregation unit 226 can retrieve the aggregated data from one or more databases 224 and cause the aggregated data to be transmitted to the interface unit 222 or network 110, for example, for presentation to a patient or physician using user device 102, 105 or 106, for example.

Tissue visualization system 100 can cause data to be displayed on interface unit 222, for example, aggregated and/or processed data providing a wound size and/or a map, visualization, or indication of oxygenation, oxyhemoglobin, deoxyhemoglobin, perfusion, water, bacterial presence and/or other indicia that may suggest abnormalities of tissue health in surface tissues. Patients and physicians can engage with an interface unit to view or analyze the indicia.

Tissue visualization system 100 can cause data, for example, aggregated data, processed data, imaging data, and/or data providing a wound size and/or a map, visualization, or indication of oxygenation, oxyhemoglobin, deoxyhemoglobin, perfusion, water, bacterial presence and/or other indicia that may suggest abnormalities of tissue health in surface tissues, to be transmitted to one or more external systems 106, such as via network 110.

For example, tissue visualization system 100 can receive imaging data from a plurality of tissue imaging systems 105, process and/or aggregate the data using data processing unit 220 and/or aggregation unit 226, and cause the data to be routed, via one or more networks 110, to, e.g. the appropriate physician (e.g., family doctor) for evaluation. The physician may be engaged with a user device 102, an external system 106, or a tissue imaging system 105.

A user device 102 may receive, process, and/or aggregate data from a plurality of tissue imaging systems 105 and/or corresponding to a plurality of patients or tissue measurements. User device 102 may receive instructions for computation from one or more external systems 106 or tissue imaging systems 105.

Tissue visualization system 100 can connect to various components, including user device 102, tissue imaging system 105, external systems 106, external database 216, in various ways including directly coupled and indirectly coupled via network 110 (which may comprise multiple networks). Each of these components can connect to each other in various ways including directly coupled and indirectly coupled via network 110 (or multiple networks).

Figure 3:
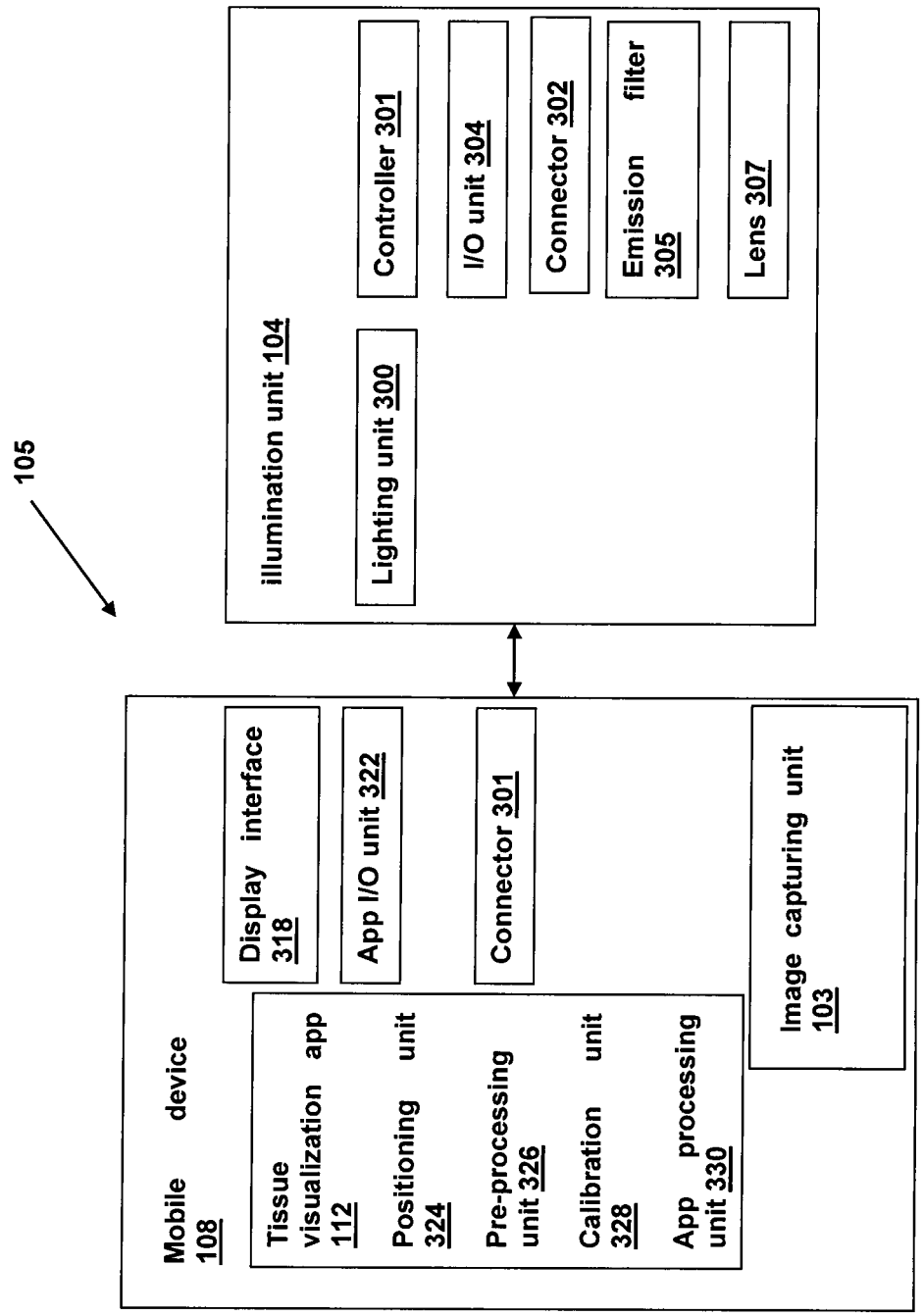
FIG. 3 depicts a view of an example of the illumination unit and a computing device according to some embodiments.

FIG. 3 depicts a view of an example of tissue imaging system 105 comprised of the illumination unit 104 and computing device 108 (e.g., a mobile device 108) comprising an internal image capturing unit 103 and installed tissue visualization app 112, according to some embodiments.

A tissue imaging system 105 is associated with an image capture unit 103. The image capture unit 103 may comprise a smartphone camera (front or back), for example.

A computing device 108 (e.g., a mobile device 108) is associated with a display interface 318. The display interface 318 can be a screen or viewfinder, for example. In some embodiments, a computing device 108 (e.g., a mobile device 108) is associated with an app I/O unit 322 that may facilitate data transmission between an illumination unit 104 and the computing device 108.

An illumination unit 104 may be associated with a computing device 108, for example, through a physical connector 302 that attaches the illumination unit 104 to the computing device 108, such as mobile device 108. An illumination unit 104, which acts as an external flash-generating device, is associated with a lighting unit 300, which may include multiple light sources 300. The light units 300 may be arranged in a circle on illumination unit 104, for example. In an example embodiment, light units 300 are arranged in a circular configuration around a central aperture.

In some embodiments, an I/O unit 304 associated with the illumination unit 104 may facilitate data transmission between the illumination unit 104 and the computing device 108. For example, I/O unit 304 may send and receive data from an app I/O unit 322. I/O unit 304 and app I/O unit 322 may implement connectivity via Bluetooth, a cable (e.g., USB, lightning, audio jack), WiFi, near-field communication, optic or optoelectronic coupling, or other means. This communication can facilitate synchronization of the lighting unit 300 and the data capture by image capture unit 103, for example, in accordance with an illumination schema that can account for various types of external illumination.

A controller 301 causes light sources to flash in a predetermined fashion. The controller 301 can receive commands from I/O unit 304 or be triggered manually (e.g., using a button). The controller 301 can be based on any type of general-purpose microprocessor or microcontroller, a digital signal processing (DSP) processor, an integrated circuit, a central processing unit (CPU), a graphics processing unit (GPU), a field programmable gate array (FPGA), a reconfigurable processor, a programmable read-only memory (PROM), or any combination thereof. In an example embodiment, the controller 301 is based on a microcontroller.

In some embodiments, the lens 307 covering the light sources 300 can be used to homogenize the light distribution on the target area. In an example embodiment, the Fresnel lens is used. The focal length of the lens can be chosen in the range 80-120% of the working distance between the illumination unit 104 and the target area. In the preferred embodiment, the focal length of the lens is equal to the working distance. Such a focal length tends to create a homogeneous illumination light distribution on the target area, which tends to result in more optimal use of dynamic range and higher accuracy of measurements on periphery of the target area.

For bacterial burden measurements, the emission filter 305 covers the image capturing unit 103 (e.g., the camera of a smartphone) to block the excitation illumination at 405±10 nm. In an example embodiment, the emission filter is attached to the illumination unit 104. In some embodiments, the emission filter 305 is a long pass filter with cut-on wavelength 450±25 nm. In some embodiments, the emission filter is a band pass filter with the transmission in the 425-750 nm range, which has the lower cut-on wavelength in the 450±25 nm range.

Computing device 108 (e.g., a mobile device 108) supports a tissue visualization application 112. Computing device 108 may run on any suitable operating system such as iOS, Android, or Windows. The tissue visualization app 112 can help position the computing device, e.g. a smartphone, at a proper distance to a target area; can synchronize flashes from an illumination unit 104 with the image capturing unit 103; can cause or coordinate the capture of a set of images; can cause or facilitate local processing of the images or of data captured; can cause capturing target area info (e.g., location, laterality, description, wound size, tissue type, patient ID, etc.); can cause or facilitate the extraction, creation, and/or aggregation of data providing a map, visualization, or indication of oxygenation, oxyhemoglobin, deoxyhemoglobin, perfusion, water, bacterial presence and/or other indicia that may suggest abnormalities of tissue health in surface tissues; can cause or facilitate storing data on computing device 108; and can cause or facilitate data to be transmitted over one or more networks 110.

The tissue visualization app 112 includes a positioning unit 324, pre-processing unit 326, calibration unit 328, and app processing unit 330.

Positioning unit 324 can cause or facilitate the positioning of the image capture unit 103 in relation to an area of patient tissue targeted for measurement.

For example, in some embodiments, positioning unit 324 can use a reference (or self-reference) object (e.g., a white circle, square, rectangle, or another shape, colour, or object) on the target area, where the reference (or self-reference) object and target area can be imaged through a viewfinder or screen associated with the, for example, mobile device 108. In some embodiments, the positioning unit 324 can recognize the reference object and cause an overlay to be presented on the display interface 318.

In some embodiments, the overlay can be marks, lines, arrows, shapes, and/or other attributes that can be used by a person engaged with the display interface 318 to move the computing device 108 (e.g. mobile device 108), for example, forwards and/or backward to create appropriate positioning of the image capture unit 103. The tissue visualization app 112 can adjust the presentation of the overlay on the display interface 318 in relation to the presentation of the reference object or tissue on the display interface 318. This may help guide the user's movement of the image capture unit 103 or computing device 108 (e.g., a mobile device 108) to achieve proper positioning of the image capture unit 103 or computing device 108 (e.g., mobile device 108) in relation to the area of patient tissue targeted for measurement.

In some embodiments, the overlay presented on the display interface 318 can be of a predetermined size and presented at predetermined locations on the display interface 318.

In some embodiments, positioning unit 324 can use the size of the reference object to trigger automatic data capturing when the computing device 108 (e.g. mobile device) or image capturing unit 103 is at a certain distance from the target area.

In some embodiments, positioning unit 324 can guide a user to move the computing device 108 (e.g. mobile device), for example, forwards and/or backward to create appropriate positioning of the image capture unit 103, by graphical, text or voice commands.

In some embodiments, reference objects may be used to facilitate calculation of a distance from a wound and/or to rescale images or measurement data.

In some embodiments, image capture unit 103 may be positioned at a proper distance from a target area, for example, a wound, by other means such as using a rangefinder or ruler.

The tissue visualization app 112 may help control the illumination of the patient tissue targeted for measurement and/or the illumination of one or more images captured by image capture unit 103 to help ensure the illumination is stable and/or predictable. The intensity of illumination may depend on the distance of the image capture unit 103 to the target area and the stability of, for example, intensity of the light source, e.g. LED, which may degrade with time or within a battery cycle. Control of such factors may be facilitated by pre-processing unit 326. For example, the tissue visualization app 112 may use a self-reference object (e.g., white or gray circle) that is placed within a target area to measure the intensity of each wavelength in each flash and recalibrate each measurement accordingly. A single measurement can include multiple flashes and wavelengths.

In some embodiments, the pre-processing unit 326 can compare the intensity of a self-reference object in the target image with the intensity of the same region in the reference image and uses the ratio between the two to scale the intensity of the target image pixel-by-pixel.

For reflectance images, app processing unit 330 can process image data captured by image capture unit 103 and pre-processed by pre-processing unit 326. For example, the user or app processing unit 330 can compare one or more images or patient measurements of a suspicious area to one or more images or patient measurements of a non-affected area.

An observation may consist of one or more measurements on a patient. The one or more images or patient measurements of a non-affected area (control sites) can be used to establish a baseline for a particular patient. Ideally, one can select a control site as a spot with intact skin symmetrical with respect to the spinal cord (e.g. on another extremity) to the suspicious area (this may be another extremity; for example, if the left ankle of a person is affected, then the right ankle may be selected as the control site). However, if it is not possible (e.g., limb amputation or widespread ulcers), then other locations (e.g., antecubital fossa) can be used as a control site. In the case of a single measurement (e.g., suspicious area only), the suspicious area readings can be compared with an area on the same image distant from the suspicious area.

In some embodiments, tissue visualization app 112 can compare an image of a suspicious area to one or more images of control sites. The tissue visualization app 112 can process an image and can also operate in video mode to process a series of images or video frames.

App processing unit 330 can use the data captured by image capture unit 103 to facilitate the extraction, creation, and/or aggregation of data providing a map, visualization, or indication of oxygenation, oxyhemoglobin, deoxyhemoglobin, perfusion, water, bacteria presence, and/or other indicia that may suggest abnormalities of tissue health, for example, in surface tissues.

The outcome of the system can be a false color or grayscale 2D map of tissue health indicators. These maps can be presented via the display interface 318 and/or transmitted over one or more networks 110, for example, to a tissue visualization system 100 or a user device 102. For example, levels of oxygenation and perfusion can highlight areas with abnormal blood supply, namely ischemic (significantly reduced perfusion and oxygenation) and angiogenic (increased perfusion) areas. A trained physician will be able to interpret these 2D maps to assess the significance of findings and decide on next steps, for example, requesting further study, monitoring progress, or dismissing the matter.

App processing unit 330 can cause the processed data to be presented via display interface 318 and/or transmitted over a network 110.

In some embodiments app processing unit 330 can use Machine Learning (ML)(including supervised ML and unsupervised ML) to extract information from collected images and other data. In particular, app processing unit 330 can build and train models, which can discriminate between various conditions and provide users with additional information. In some embodiments, the app processing unit 330 uses convolutional neural networks for automatic or semi-automatic detection and/or classification of the skin or wound conditions. In some embodiments, ML models can be built and trained using other tools (e.g., the data processing unit 220) and deployed to app processing unit 330 for image/data detection/classification.

Figure 4:
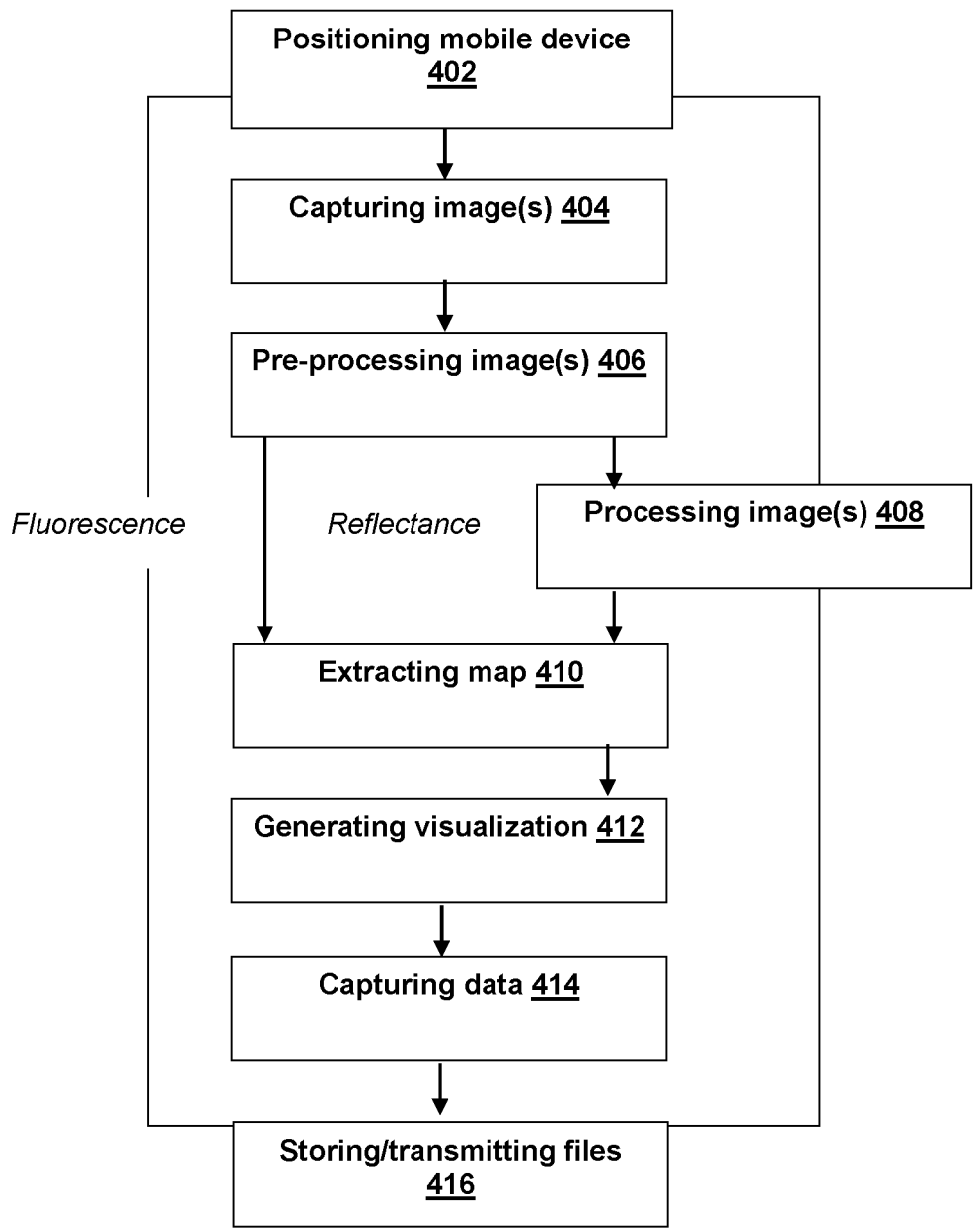
FIG. 4 depicts a flowchart of an example method for capturing measurements and visualizing tissue according to some embodiments.

FIG. 4 is a flowchart of an example method for capturing measurements and visualizing tissue according to some embodiments.

At 402, a computing device 108 (e.g. a mobile device 108) is positioned at a proper distance (working distance) in relation to an area of tissue (e.g., using a positioning unit 324). In some embodiments, the computing device 108 or image capturing unit 103 is positioned 10-30 cm from the tissue. In an embodiment, the image capturing unit 103 is positioned 10-15 cm from the tissue.

At 404, image capture unit 103 in conjunction with illumination unit 104 captures a measurement of tissue according to an illumination schema.

At 406, in some embodiments, pre-processing unit 326 preprocesses the measurement data by a) registering (aligning) images to avoid camera motion artifacts, b) subtracting image with no illumination from images with illumination to account for the presence of an ambient light.

In some embodiments, the step 406 may include any or all additional steps: c) recalibrating each measurement accordingly in order to control parameters related to the intensity of illumination, d) dividing the intensity images on reference images to obtain normalized images, e) flattening the images. In other embodiments, the filtering and frequency domain processing (e.g. fast Fourier transformation) may be used additionally for denoising.

Recalibration of each measurement using a self-reference object may take into account any possible drift or degradation of illumination light intensity, which will tend to improve the quality of results.

Dividing the intensity images on reference images may take into account the heterogeneity of illumination light distribution on a target area, resulting in normalized images that tend to improve quality of results.

Imaging of body parts with high curvature (for example, heels or toes) can pose a significant clinical challenge. Different parts of the target area are on different distance from the illumination unit and the camera, and since the camera registers light intensity that depends on that distance, the curvature(s) can negatively affects accuracy of measurements or may produce erroneous results. In an embodiment, the step of flattening images is to take into account the reflection of light from curved surfaces. This can be achieved by plurality of methods. In some embodiments, approximation of the shape of the body part and rescaling normalized image to compensate for these deviations from the working distance is used. In other embodiments, shape fitting (for example, spherical, ellipsoidal, or cylindrical) may be used.

In some embodiments, registration (alignment) of images can be done using phase correlation or block matching algorithms (e.g., using a self-reference object).

In some embodiments, recalibration can be done by pre-processing unit 326 using a self-reference object to measure the intensity of each wavelength in each flash.

In some embodiments, any or all steps after the step 406 can be skipped.

In some embodiments, app processing unit 330 can cause transmission over network 110 of data, such as pre-processed images after step 406. In this case, upon receipt of the data, data processing unit 220 of tissue visualization system 100 may extract and visualize tissue health indicators.

At 408, app processing unit 330 processes the images to extract information, such as concentrations of tissue chromophores. In some embodiments, app processing unit 330 extracts indications of oxyhemoglobin and deoxyhemoglobin. In some embodiments, in addition to oxy- and deoxy-hemoglobin, app processing unit 330 extracts the indication of melanin. In some embodiments, app processing unit 330 additionally extracts water content indications.

In some embodiments, indications of oxyhemoglobin, deoxyhemoglobin, and water can be extracted directly from the obtained images using a Beer-Lambert or modified Beer-Lambert model.

In an exemplary embodiment, an additional step is taken to extract tissue absorption coefficients from the obtained images using a tissue optical model (or a tissue light propagation model). A tissue optical model would link the reflected signal with optical properties of the tissues, namely coefficients of absorption and scattering. Various light propagation models (for example, diffuse approximation model) can be used to extract such relationship. The appropriate model can be selected based on acceptable accuracy vs. computational intensity considerations.

In some embodiments, the least squares fitting, or LSF (with or without regularization) can be used to extract the concentration of each chromophore. In some embodiments, LSF extracts indications of chromophores directly from the obtained images. In an exemplary embodiment, LSF is applied after extraction of indication of absorption coefficient using the tissue light propagation model.

In other embodiments, other curve fitting methods (for example, least absolute deviations) may be used to extract indications of chromophores.

At 410, app processing unit 330 extracts indicia that allows the tissue health indicators of the imaged tissue to be presented. For example, the indicia may allow the oxygenation and/or perfusion to be presented as a map.

In some embodiments, app processing unit 330 can send to the network 110 data from the step 408. In this case, data processing unit 220 will visualize tissue health indicators.

At 412, tissue visualization app 112 generates a visualization of the tissue health indicators of the imaged tissue and causes the visualization to be presented via the display interface 318.

In some embodiments, computing device 108 comprises a graphical user interface displayed on display interface 318 by app processing unit 330. At 414, the tissue visualization app 112 collects data related to the image (e.g., patient ID, laterality, location, diagnosis, comments, measurements). In some embodiments, a speech-recognition system is used to collect data.

At 416, tissue visualization app 112 causes a results file of the data or indicia to be stored and/or transmitted, for example, over a network 110 to a user device 102, tissue visualization system 100, and/or external system(s) 106.

Figure 5:
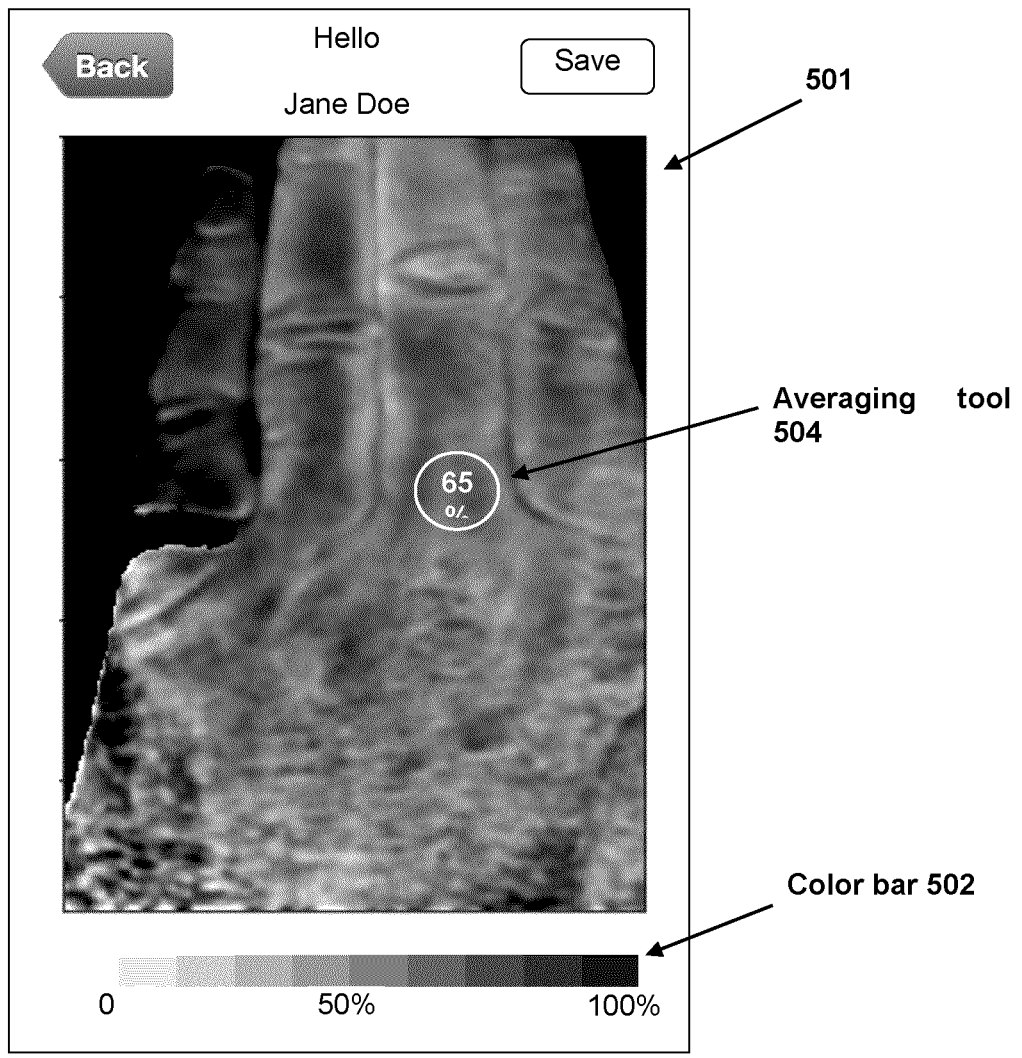
FIG. 5 depicts a view of an example interface for visualizing tissue according to some embodiments.

FIG. 5 is a view of an example interface for visualizing tissue according to some embodiments.

In some embodiments, a color bar 502 can be implemented to guide the user when viewing the image.

In some embodiments, the averaging tool 504 (which averages tissue health index within a defined area) can be implemented to assist the user. In some embodiments, the averaging tool 504 can be a small circle on a touchscreen, such as the relatively small area shown in FIG. 5.

Figure 6:
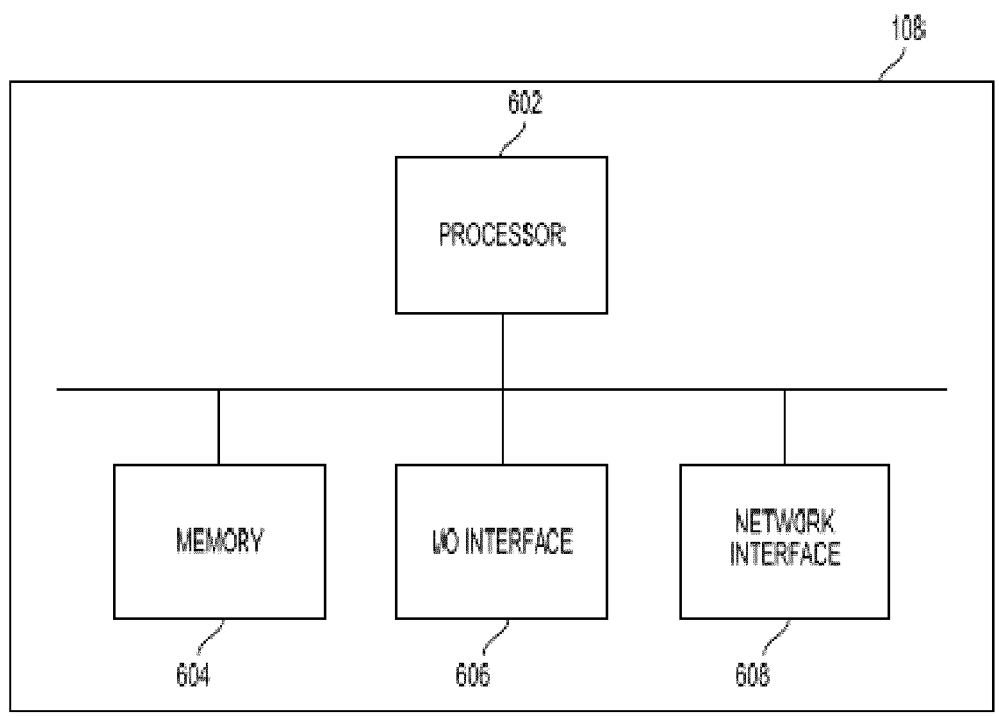
FIG. 6 depicts a diagram of an example architecture of a computing device according to some embodiments.

FIG. 6 is a schematic diagram of an exemplary embodiment of computing device 108. As depicted, computing device 108 (e.g. mobile device 108) includes at least one processor 602, memory 604, at least one I/O interface 606, and at least one network interface 608.

Each processor 602 may be, for example, any type of general-purpose microprocessor or microcontroller, a digital signal processing (DSP) processor, an integrated circuit, a central processing unit (CPU), a graphics processing unit (GPU), a field programmable gate array (FPGA), a reconfigurable processor, a programmable read-only memory (PROM), or any combination thereof.

Memory 604 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM), or the like.

Each I/O interface 606 enables computing device 108 (e.g., a mobile device 108) to interconnect with one or more input devices, such as a keyboard, mouse, camera, touch screen, and a microphone, or with one or more output devices such as a display screen and a speaker.

Each network interface 608 enables computing device 108 (e.g., a mobile device 108) to communicate with other components, to exchange data with other components, to access and connect to network resources, to serve applications, and perform other computing applications by connecting to a network (or multiple networks) capable of carrying data.

Computing device 108 is operable to register and authenticate users (using a login, unique identifier, and password, for example) prior to providing access to applications, a local network, network resources, other networks, and network security devices. Computing devices 108 may serve one user or multiple users.

Figure 7:
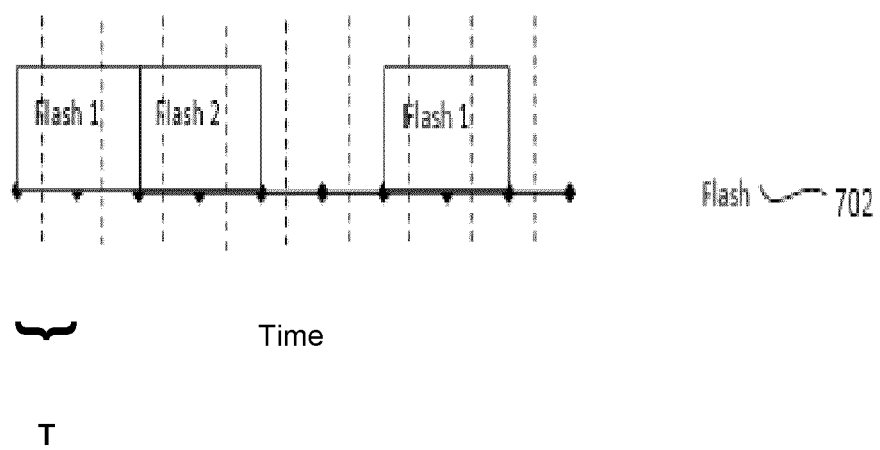
FIG. 7 depicts an example of illumination and image capturing scheme according to some embodiments.

FIG. 7 is an example of an illumination and image capturing schema according to some embodiments. Other illumination and image capturing schemas can be used. In order to account for external illumination, the example image capturing/illumination schema in FIG. 7 has been developed.

FIG. 7 plots the flash 702 coordinated by illumination unit 104, as a function of time. Computing device 108 (e.g., a mobile device 108) uses the synchronization of flash if the illumination unit 104 is used to provide the external flash. As shown at 702, the illumination schema (cycle) consists of m flashes (with m=2 in the example of FIG. 7) and one period without flash, with n/4≤m≤n, where n is the number of wavelengths. Cycles can be repeated continuously during video mode capturing.

The exposure time (T) for each frame (in milliseconds) can be selected as T=k/2*f, where k is an integer, and f is the utility frequency for a particular country in Hz (e.g., 60 Hz for North America, 50 Hz for Europe). In a video mode, the framerate can be selected as fps=2*f/k (e.g., 30, 24, 20, 15, 12, and 10 fps for North America and 25, 20, and 10 fps for Europe). The frame rate of 20 fps (T=50 ms) is an example selection. It can work without any configurations with external light sources connected to any electrical grid (50 Hz or 60 Hz). Other frame rates can also be used.

The duration of each flash can be T or any whole number multiple of T. This arrangement facilitates easy optical synchronization between illumination unit and image capturing unit. For example, the cycle consists of m back to back flashes with duration 2T milliseconds each, followed by no lit period 2T milliseconds long, as shown in the plot 702.

In some embodiments, computing device 108 (e.g. mobile device 108) associated with an illumination unit 104 may use the same frame to capture an image illuminated at 2, 3, or 4 wavelengths, which can be captured by different color wavelengths of an RGB camera (e.g. 480 and 660 nm, which will be captured by blue and red wavelengths, respectively) or an RGB-NIR camera.

Figure 8:
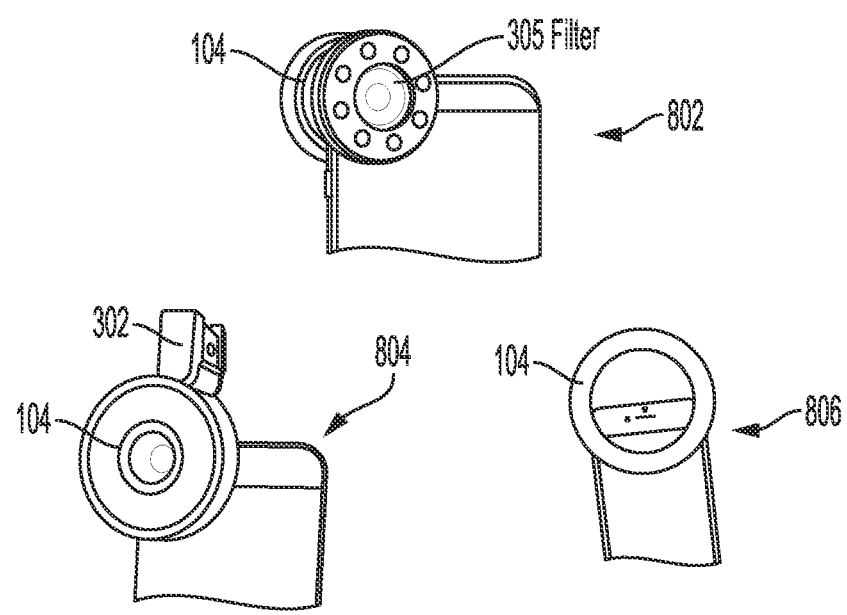
FIG. 8 depicts a view of example illumination units according to some embodiments.

FIG. 8 is a view of example illumination units according to some embodiments.

An illumination unit 104 can be an external flash device that can be attached to a computing device 108, for example, a smartphone. In some embodiments, it can be synchronized with a tissue visualization app 112 or computing device 108 (e.g., a mobile device 108) using Bluetooth or other connectivity. In some embodiments, the illumination unit 104 can be built into a case for a computing device 108 (e.g., a mobile device 108). In some embodiments, the illumination unit 104 receives power from the computing device 108 (e.g., a mobile device 108) or an external source (e.g., wall charger).

In some embodiments, illumination unit 104 comprises a battery. The illumination unit 104 can also be chargeable using a standard micro USB port, wirelessly or by way of inductive charging.

The illumination unit 104 can be used with a front- or back camera of a mobile device 108, for example. Illumination unit view 806 illustrates an illumination unit 104 used in conjunction with a front-facing camera of a user computing device 108.

In some embodiments, the illumination unit 104 can be optimally designed to associate with a computing device 108 (e.g. mobile device 108) by way of a clip or other means 302 that can be attached to the computing device 108 (e.g. mobile device 108) with the thickness of up to 15 mm, as shown in views 802 and 804.

In an example embodiment, illumination unit 104 uses a compression clip that can be attached to the computing device 108 (e.g. mobile device 108), with the thickness up to 15 mm, as shown in view 802. In some embodiments, the illumination unit 104 can be mounted using a spring clip, as shown in views 804 and 806.

The illumination unit 104 can produce a sequence of flashes of predetermined length. A wavelength can refer to light sources shining at the same wavelength, or the possibility of multiple wavelengths shining in a single flash. Each of the flashes may shine at 1-4 particular wavelengths.

The illumination unit 104 can use narrow band high-efficiency light sources 300, such as LEDs. The light source in the illumination unit 104 may contain single wavelength or multi-wavelength LEDs.

As shown in view 802, the light sources 300 can be arranged in a circle, with a center close to the center of a camera 103 of computing device 108 (e.g. mobile device 108).

In some embodiments, each wavelength can consist of two or four light sources 300, arranged in a symmetrical pattern on an illumination unit 104 (e.g., every 180 or 90 degrees on a circle).

For oxygenation measurements, the illumination unit 104 can use two or more wavelengths in the range of 450-750 nm. For measurements of oxygenation and perfusion and the compensation of skin color (melanin), the illumination unit 104 can use three or more wavelengths in the range of 450-750 nm. In an example embodiment, 450-650 nm range is used.

Wavelengths can be selected from one or more of the following regions: a) biggest discrimination in light absorption between oxy- and deoxyhemoglobin: 450-500 nm and 600-750 nm, b) isobestic points (e.g., 510±10 nm, 525±10 nm, and 590±10 nm), c) largest absorption by oxy- and deoxyhemoglobin: 540-580 nm.

For water content measurement in addition to two or more wavelengths in 450-750 nm (or preferably 450-650 nm) range a wavelength of 970±10 nm is used.

For bacterial burden measurements, a wavelength of 405±10 nm is used. In some embodiments, it can be combined with two or more wavelengths in 450-750 nm (or preferably 450-650 nm) range, which captures reflectance images.

For bacterial burden measurements, the illumination unit 104 or image capture unit 103 may contain emission filter 305. In an example embodiment, the emission filter is attached to the illumination unit 104. In some embodiments, the emission filter 305 is a long pass filter with cut-on wavelength 450±25 nm. In some embodiments, the emission filter is a band pass filter with the transmission in the 425-750 nm range, which has the lower cut-on wavelength in the 450±25 nm range.

The illumination unit 104 can be synchronized with an image capture unit 103 of computing device 108 (e.g. mobile device 108) to produce an illumination schema. The illumination unit 104 associated with an image capture unit 103 can follow an illumination schema where each wavelength shines sequentially (n=m, where n is the number of wavelengths, m is the number of flashes in one cycle).

In some embodiments, lighting unit 300 configured to engage with a computing device 108 (e.g. mobile device 108) or image capture unit 103 may have the following example implementations:
- the lighting unit 300 may provide light from sources arranged in a circle or otherwise;
- the lighting unit 300 may use two, four or another number of light sources per wavelength;
- the lighting unit 300 may use light sources with central wavelength 405±10 nm for bacteria imaging;
- the lighting unit 300 may use an additional 750-1000 nm range for user devices 102 without an IR filter on camera (e.g., front-facing camera on a smartphone);
- the lighting unit 300 may use light sources with a central wavelength of 970±10 nm for water imaging for user devices 102 without an IR filter on camera (e.g., front-facing camera on a smartphone);
- the illumination unit 104 and/or lighting unit 300 and a computing device 108 (e.g. mobile device 108) can be mounted on an extension device (e.g., on a selfie stick);
- the imaging unit 104 can be associated with an external lens (e.g., macro lens), emission filter, polarizer, or not.

In some embodiments, illumination unit 104, for example, including a multispectral external flash, can be operable with an image capture unit 103 or another recording device. For example, illumination unit 104 may be integrated with a personal computer, tablet, or otherwise.

The systems described tends to offer distinct advantages. For example: the flash design may be used with any computing device 108, such as a smartphone (iOS, Android, etc.) of any shape; the flash/image capturing schema, may allow measurements in any type of ambient light and with any type of smartphone; self-calibration using a self-reference object increases accuracy; proper positioning of the camera (distance from the wound) is facilitated by use of a self-reference object (e.g. a circle); and the illumination schema produces reproducible and homogeneous illumination. The above-noted expected advantages are examples of advantages and may not comprise all advantages of the present systems/devices.

The system can also tend to overcome challenges, for example, of building the flash, in the case for a smartphone, such as a challenge that each smartphone can have its own form-factor and thus would require multiple cases to be built at least for the most popular models. Other challenges that the system may overcome, or benefits of the system, include:
- use of IR filter on some smartphone cameras. These filters, which are used to improve the quality of pictures, filter out light with wavelengths over 750 nm and are being used mostly on more expensive smartphones. Typical pulse oximetry schemas employ 660 and 900 nm bands. Thus, these schemas cannot be employed universally on smartphones.
- Connection to a plurality of existing EHR systems.
- Motion artifacts (e.g., due to tremor) while taking measurements.
- The flickering, high dynamic range, etc. that may result from taking images in various light conditions (e.g., indirect sunlight, office light, observation room, etc.) is combatted.
- Flickering caused by the various utility frequencies in different countries.
- Producing predictable light distribution, not very sensitive to slight misplacements of the flash or the smartphone.
- Difficulty in synchronizing the phone and external flash.
- Use of the lens (e.g., Fresnel lens) covering the light sources homogenizes the light distribution on the target area, thus extending dynamic range and increasing the accuracy of measurements.
- use of multiwavelength LEDs (e.g., RGB LEDs) creates the similar intensity distribution for each wavelength and saves space on the illumination unit.
- The intensity of illumination can vary, for example, based on the distance to a target area and the stability of LED intensity (e.g., LED intensity may change with time, temperature, or within battery cycle). In particular, the intensity of illumination light on the surface of the tissue drops as an inverse square with the distance from the illumination unit to the target area. Thus, increasing working distance by 50%, will cause drop of illumination intensity by 55%, and so the system can compensate by capturing the intensity of illumination at the revised working distance and normalizing images on these values.
- porphirin and pyoverdine have an absorption peak in Soret band, where oxyhemoglobin and deoxyhemoglobin have absorption peaks as well. The presence of a blood component may significantly impact porphyrin/pyoverdine emission. True fluorescence intensity can be deconvoluted using known oxyhemoglobin and deoxyhemoglobin concentrations.
- Ability to change or upgrade components of the system independently. For example, a user can use his or her own smartphone as a computing device, and upgrade such device with updated versions without a necessity to buy a whole new system.

A tissue imaging system 105 can be used in a variety of applications, including in the following scenarios.

Use case 1: A doctor at a hospital during a physical exam of a patient in acute care has found a suspicious wound on the leg. The patient has diabetes, so the MD has a suspicion that it can be a non-healing DFU. The current standard of care for this is angiography, which is not available in his community hospital. It will cost around $20,000 for the procedure and arrangement of medical transportation to/from another hospital. However, using the device the doctor can screen the wound on the spot and see whether it is ischemic (and require angiography for proper assessment) or nonischemic (and will heal well without any extra efforts).

Use case 2: A family doctor during an annual checkup has found a suspicious wound on a patient's leg. The patient has diabetes, so the MD has a suspicion that it can be a non-healing DFU. The current standard of care for this is angiography. However, it can be performed in major hospitals only. It is associated with $1,500 per procedure (in the US) or waiting time (for example, 41 days in Ontario, Canada). Using the device, the doctor can screen the wound on the spot and see whether it is ischemic (and require angiography for proper assessment) or nonischemic (and will heal well without any extra efforts).

Use case 3: A family doctor during an annual checkup has found a suspicious wound on a patient's leg. The patient has diabetes, so the MD has a suspicion that it can be a non-healing DFU. The current standard of care for this is angiography. It can be performed in major hospitals only. It is associated with $1,500 per procedure (in the US) or waiting time (for example, 41 days in Ontario, Canada). Using the device, the doctor captures images of the wound on the spot. However, such as he does not have significant experience in wound care, he decides to send images to a podiatrist, who provides him with an assessment of whether it is ischemic (and requires angiography for proper assessment) or nonischemic (and will heal well without any extra efforts). The doctor accordingly refers the patient to the podiatrist.

Use case 4: A nurse is attending a small rural community. During an exam of a patient, she has found a suspicious ulceration near the small toe. She has a suspicion that it can be a peripheral arterial disease. She uses the device to take a snapshot of the wound and sends images to a family physician (if the patient has one) or a podiatrist. The doctor reviews the images and provides guidance within a few hours. The nurse instructs the patient on further actions.

Use case 5: A medical nurse is attending a small long-term residence. During an exam of a patient, she has found a suspicious ulceration near the big toe. She has a suspicion that it can be a peripheral arterial disease. She uses the device to take a snapshot of the wound and sends images to a family physician (if the patient has one) or a podiatrist. The doctor reviews the images and provides guidance within a few hours. The nurse instructs the patient on further actions.

Use case 6: A senior with diabetes finds a suspicious cut on his heel. He is aware of the dreadful consequences of DFU, so he decides to buy the device in a drugstore. With the help of his wife he takes images of the wound and sends them to his family doctor. The doctor makes an assessment and advises the patient within a few hours.

Use case 7: A senior with diabetes finds a suspicious cut on her forefoot. She is aware of the dreadful consequences of DFU, and tells her concerns to her daughter. Her daughter bought a flash attachment 104 in a drugstore, attaches it to her smartphone 108, downloads the tissue visualization app 112, and takes images of the wound. As her mother does not have a family doctor, she sends the images to a podiatrist. The doctor makes an assessment and sends a referral within a few hours.

Use case 8: A family doctor during an annual checkup of a patient finds a suspicious mole. Using the device, he can screen the mole on the spot and see whether it is suspicious (has increased blood supply and requires additional study) or not suspicious.

Use case 9: The nurse in a long-term care facility checks a bed-bound patient for potential pressure ulcers. Using the device, she can screen bony prominence areas to determine if any are suspicious.

Use case 10: An advanced wound care nurse cleanses an existing wound. She uses the device to visualize bacterial presence and to guide debridement.

Use case 11: A nurse takes a swab from an existing wound. She uses the device to visualize bacterial presence and to guide swabbing.

The accuracy of measurements can be improved if the light intensity distribution produced by illumination unit 104 is known. In an example embodiment, to capture light intensity distribution produced by illumination unit 104, a reference image is used.

Figure 9:
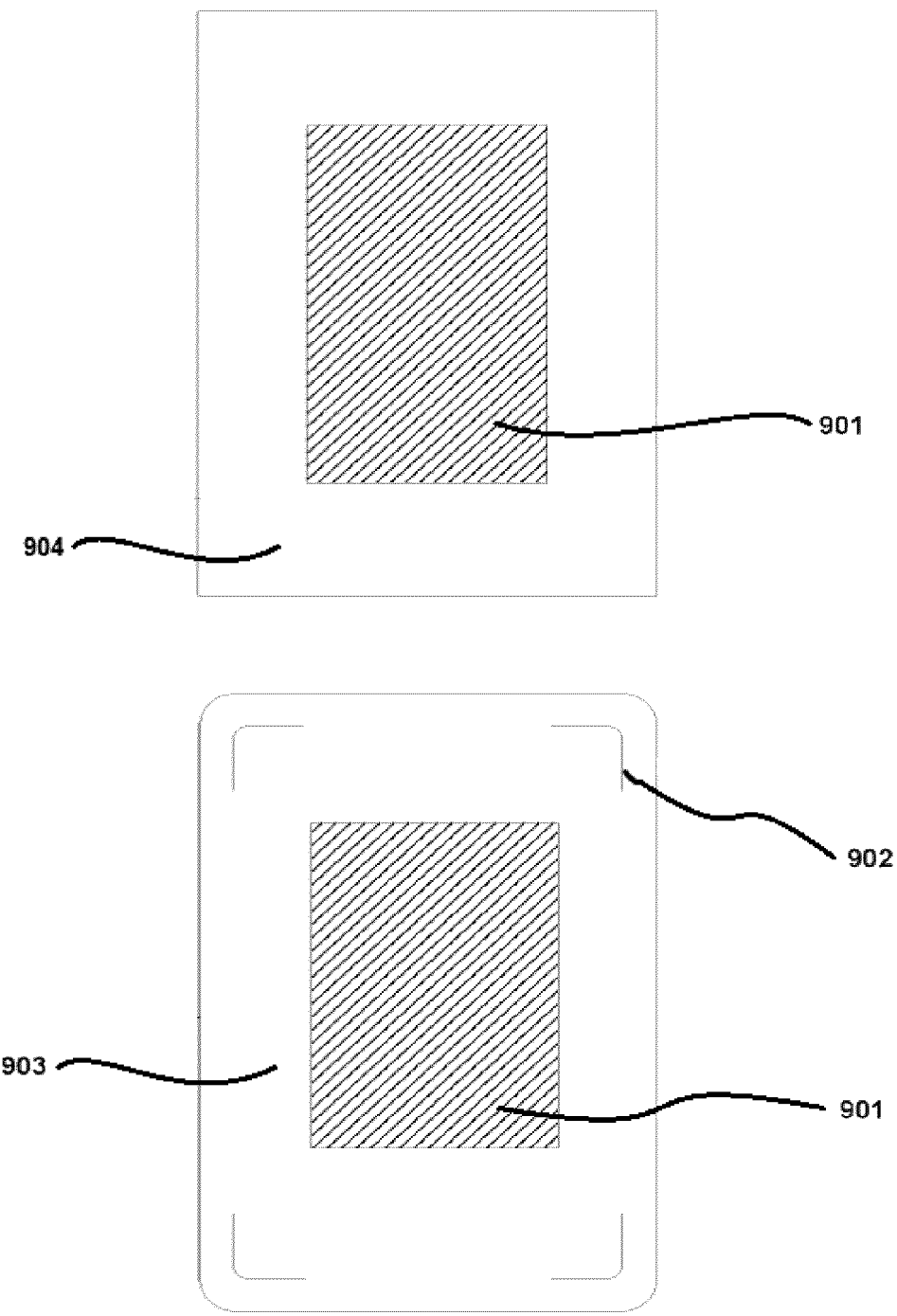
FIG. 9 depicts an example of the workflow used to take reference images.

With reference to FIG. 9, example features used for capturing reference images are depicted. In some embodiments, the reference image can be captured by calibration unit 328 of tissue visualization app 112 and then used by the tissue imaging system 105 or tissue visualization system 100 to obtain a processed measurement 501 (an example of which is shown in FIG. 5).

The reference image is captured using a reference object 901. Reference object refers to an object with known homogeneous optical properties (e.g., spectral dependence of reflectance). Reference object 901 can be various shapes, such as a circle or rectangle. In an example embodiment, reference object 901 is a rectangle with an aspect ratio of 4:3. Various colors can be used for reference object 901, such as white or gray (for example, an 18% gray rectangle on a white background 904, such as a white sheet of paper).

In one embodiment, screen markers 902 displayed on a screen 318 of the computing device 108 (e.g. mobile device 108) can define a target area 903 which can be used to position the device an optimal distance away from the reference object 901. The computing device 108 should be positioned such that screen markers 902 line up with the reference object 901 to ensure an optimal image-capturing distance is achieved. Other distance measuring devices, such as a rangefinder or ruler, can be used to position device at the optimal distance. In an example embodiment, object recognition by tissue visualization app 112 can be used to position the device at the optimal image capturing distance.

In an example embodiment, the computing device 108 (e.g., a mobile device 108) can take the required reference image automatically upon proper placement of the device. In other embodiments, the computing device 108 takes the image upon manual user initiation. In an embodiment, upon activation of the image capture unit 103, the computing device 108 takes several images. In an example embodiment, one or more images are taken with flash, and one is taken without. Alternatively, images can be taken only with flash.

The computing device 108 (e.g., a mobile device 108) can pre-process the reference image to improve the image quality. The pre-processing may comprise the following steps: a) image registration, b) image subtraction.

In some embodiments, computing device 108 (e.g., a mobile device 108) uses image registration to reduce shake during image capturing. This can be accomplished using phase correlation or block matching algorithms.

In some embodiments, computing device 108 (e.g., a mobile device 108) uses image subtraction to remove ambient light in the image. In this case, the image without external illumination (no flash) is subtracted from images with external illumination (with flash). Image subtraction is not required if only images with flash are used.

The reference image can be stored locally on the computing device 108 (e.g. mobile device 108) or remotely, for future use.

The reference image can be captured before the first measurement and at any time thereafter. There is no need to capture reference images before every measurement.

Figure 10:
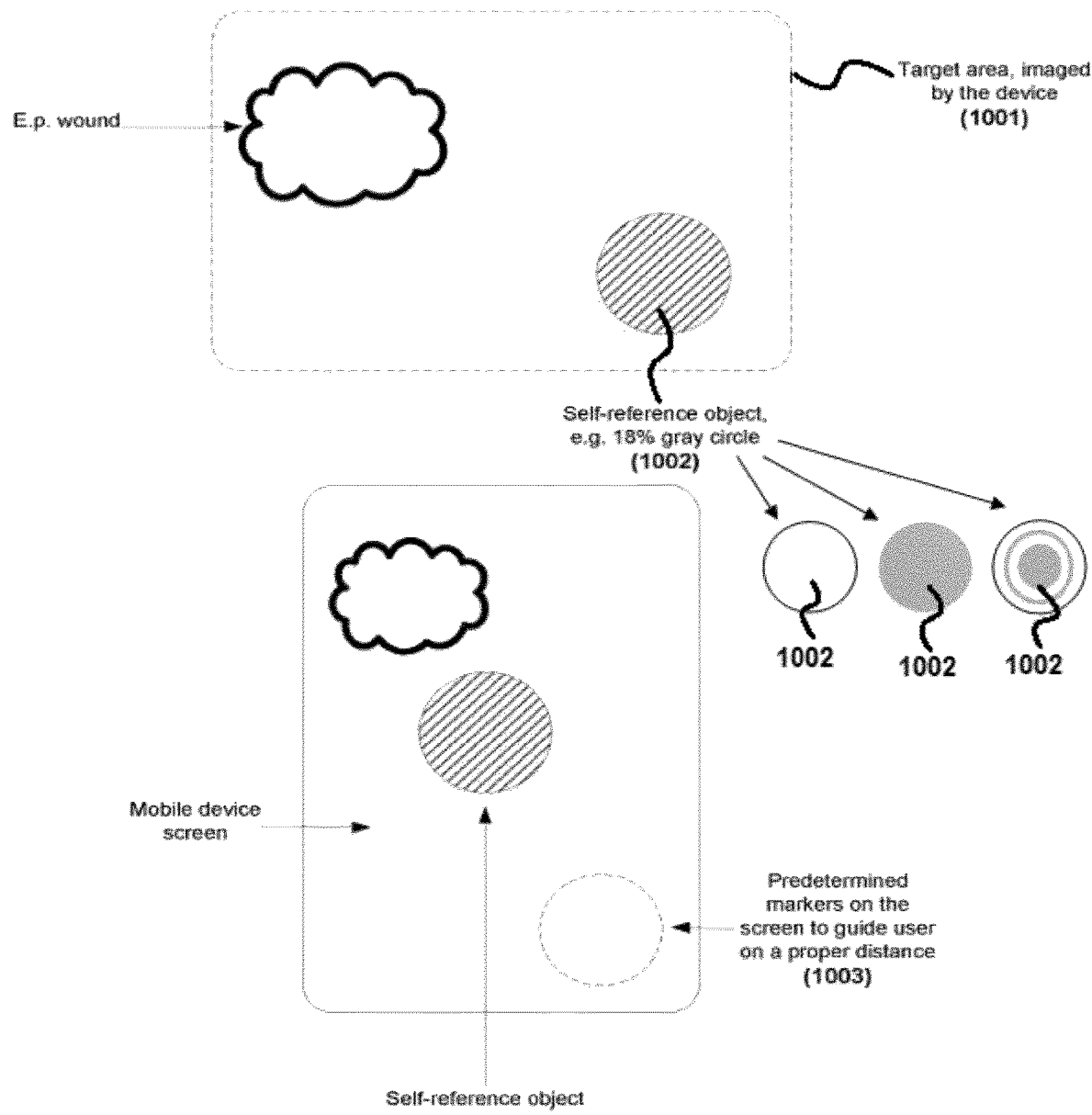
FIG. 10 depicts a view of a schematic of imaging tissue and self-reference objects.

Steps for producing measurement map 501 are now discussed, with respect to FIG. 10.

Computing device 108 (e.g. mobile device 108) is held at a specific distance away from the subject, for example a human body, in order to optimally image the area of interest.

In some embodiments, a self-reference object 1002 is used to ensure the proper distance from the human body. A self-reference object 1002 is placed within the device target area 1001 imaged by the computing device 108 (e.g., a mobile device 108). In an example embodiment, the self-reference object 1002 comprises an 18% gray circle 1-2 cm in diameter.

In some embodiments, the computing device 108 (e.g. mobile device 108) or image capturing unit 103 is moved so that a predefined screen marker 1003 is shown as the same size as self-reference object 1002 on the device target area 1001, so as to guide the user to the optimal image capturing distance.

In an example embodiment, computing device 108 (e.g., a mobile device 108) uses object recognition to trigger automatic image capturing upon a certain screen size of the self-reference object, in pixels, being achieved.

Alternatively, other means of measuring a distance, such as a rangefinder or a ruler, can be used to position the device at the proper distance from the area of interest.

Once the optimal distance from the human body is determined, computing device 108 (e.g., a mobile device 108) can take the required images. In an example embodiment, the device takes the required image automatically upon the proper placement of the computing device 108 (e.g., a mobile device 108) or image capturing unit 103. The device may take several images. In an example embodiment, one or more images will be taken with flash, and one will be taken without flash.

The device pre-processes the image in order to improve the quality of the image and measurement map 501. The pre-processing may contain the following steps: a) image registration, b) image subtraction.

In some embodiments, the device uses image registration to reduce shake. This can be accomplished through phase correlation or block matching.

In some embodiments, the device uses image subtraction to remove ambient light in the image. In this case, the image without external illumination (flash) is subtracted from images with external illumination (flash).

To further increase the quality of results, the self-calibration of each measurement using a self-reference object 1002 can be implemented. In this case the pre-processing may contain the following steps: a) image registration, b) image subtraction, c) self-calibration, and d) division on the reference image, e) flattening the images.

If the embodiment utilizes self-reference object 1002, the intensity of the image is adjusted using the self-reference object to account for any imperfections or changes in intensity. In an example embodiment, pre-processing unit 328 can compare the intensity of a self-reference object in the target image with the intensity of the same region in the reference image and use the ratio between the two to scale the intensity of the target image pixel-by-pixel.

If the embodiment utilizes previously taken reference images, the device finds the normalized image by dividing pixel-by-pixel image onto the reference image and multiplying by a known reflectance of the reference object.

In some embodiments, the tissue imaging system 105 can perform the processing of the image to obtain measurements. This can be achieved through all or some of the following steps: a) the absorption coefficient is determined from reflectance (e.g., using Beer-Lambert, or modified Beer-Lambert law); b) the chromophore concentration is determined from the absorption coefficient (e.g., using least square fitting); c) the perfusion and oxygenation is determined from the chromophore concentration (oxygenation=oxyhemoglobin/(oxyhemoglobin+deoxyhemoglobin), perfusion=oxyhemoglobin deoxyhemoglobin).

In some embodiments, the pre-processed measurement (normalized image) is taken on computing device 108 (e.g., a mobile device 108) and then sent through network 110 to the tissue visualization system 100.

Bacterial burden indicator can be used stand-alone or in combination with reflectance images. Porphyrin and pyoverdine have an absorption peak in the Soret band, where oxyhemoglobin and deoxyhemoglobin have absorption peaks as well. Thus, the presence of a blood component may significantly impact porphyrin/pyoverdine emission. With reference to FIG. 4, true fluorescence intensity can be deconvoluted using known oxyhemoglobin and deoxyhemoglobin concentrations found in step 410. In an example embodiment, a light source with the center wavelength of 405±10 nm is used in combination with 2 or 3 wavelengths from the 450-650 nm range.

Once tissue health indicators levels are found, the invention presents the color or grayscale maps through processing via tissue visualization system 100 or tissue imaging system 105. These results can be stored locally on the device or remotely. The pre-processed normalized image and the processed tissue health indicators maps can all be stored in local or remote storage.

The embodiments of the devices, systems, and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, references have been made to servers, devices, systems, units, or computing devices. It should be appreciated that the use of such terms is deemed to represent one or more computing devices having at least one processor configured to execute software instructions stored on a computer-readable tangible, non-transitory medium. For example, a server can include one or more computers operating as a web server, database server, or another type of computer server in a manner to fulfill described roles, responsibilities, or functions.

Various example embodiments are described herein. Although each embodiment represents a single combination of inventive elements, all possible combinations of the disclosed elements include the inventive subject-matter. Thus, if one embodiment comprises elements A, B, and C, and a second embodiment comprises elements B and D, then the inventive subject-matter is also considered to include other remaining combinations of A, B, C, or D, even if not explicitly disclosed.

The term "connected" or "coupled to" may include both direct coupling (in which two elements that are coupled to each other contact each other) and indirect coupling (in which at least one additional element is located between the two elements).

Part of the technical solution of embodiments may be in the form of a software product (while other required aspects, for example the image capture unit 103 and illumination unit 104, necessitate hardware). The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information.

Although the embodiments have been described in detail, it should be understood that various changes, substitutions, and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein, may be utilized. Accordingly, the appended claims are intended to include within their scope such processes, machines, manufacture, compositions of matter, means, methods, or steps.

As can be understood, the examples described above and illustrated are intended to comprise examples only.

REFERENCES

Bates-Jensen B M, McCreath H E, Kono A, Apeles N C R, Alessi C. Subepidermal moisture predicts erythema and stage 1 pressure ulcers in nursing home residents: a pilot study. J Am Geriatr Soc 2007; 55(8):1199-205.

Bates-Jensen B M, McCreath H E, Pongquan V, Apeles N C R. Subepidermal moisture differentiates erythema and stage I pressure ulcers in nursing home residents. Wound Repair Regen 2008; 16(2):189-97.

Guihan M, Bates-Jenson B M, Chun S, Parachuri R, Chin A S, McCreath H. Assessing the feasibility of subepidermal moisture to predict erythema and stage 1 pressure ulcers in persons with spinal cord injury: a pilot study. J Spinal Cord Med 2012; 35(1):46-52.

Ching C T, Chou M Y, Jiang S J, Huang S H, Sun T P, Liu W H, et al. Tissue electrical properties monitoring for the prevention of pressure sore. Prosthet Orthot Int 2011; 35(4): 386-94.

Harrow J J, Mayrovitz H N. Subepidermal moisture surrounding pressure ulcers in persons with a spinal cord injury: a pilot study. J Spinal Cord Med 2014; 37(6):719-28.

Bates-Jensen B M, McCreath H E, Pongquan V. Subepidermal moisture is associated with early pressure ulcer damage in nursing home residents with dark skin tones: pilot findings. J Wound Ostomy Cont Nurs 2009; 36(3): 277-84.

Luck W. A. P, (1974). Infrared overtone region. In W. A. P. Luck (Ed.), Structure of water and aqueous solutions, Weinheim: Verlag Chemie. pp. 248-284.

Kjeldstad B., Christensen T., and Johnsson A., Porphyrin photosensitization of bacteria, Adv. Exp. Med. Biol. 193, 155-159 (1985).

Cody Y. S. and Gross D. C, Characterization of pyoverdin (pss), the fluorescent siderophore produced by *Pseudomonas syringae* pv. *syringae*, Appl. Environ. Microbiol. 53(5), 928-934 (1987).

What is claimed is:

1. A portable illumination apparatus for facilitating visualizations of tissue, the apparatus comprising:
   a portable housing for detachable attachment proximal to an image capturing unit; and
   an illumination unit comprising one or more narrow band light sources configured to shine m flashes of light on a target area of the tissue at n predetermined wavelengths, wherein: $n/4 \leq m \leq n$; and m is a number of light flashes in one cycle and n is a number of wavelengths.

2. The portable illumination apparatus of claim 1, wherein the illumination unit further comprises a lens covering the one or more light sources, the lens having a focal length that is 80%-120% of a working distance between the illumination unit and the target area of the tissue.

3. The portable illumination apparatus according to claim 1, wherein the one or more light sources is configured to provide flashes that are at least one of:
   (i) 405±10 nm wavelength, and having at least one of: (a) a long pass filter with a cut-on wavelength of 450±25 nm or (b) a bandpass filter with transmission in a 425 nm-1000 nm range,
   (ii) two wavelengths in a 450 nm-750 nm range, at least one of which in a green range,
   (iii) three wavelengths in a 450 nm-750 nm range, at least one of which in the green range, or
   (iv) 970±10 nm wavelength.

4. The portable illumination apparatus according to claim 1, wherein the illumination unit further comprises at least one of:
   (i) a controller to control illumination of the one or more light sources, or
   (ii) a rechargeable battery for powering the apparatus.

5. The illumination apparatus according to claim 1, wherein the one or more light sources are arranged about a central aperture of the illumination unit, the central aperture having a radius of 0.5-3 cm.

6. The illumination apparatus of claim 5, wherein the one or more light sources are arranged in a ring having a radius of 1.5-6 cm.

7. The illumination apparatus according to claim 1, wherein the portable housing comprises a compression clip or a spring clip for mounting the apparatus on at least one edge of a mobile device and proximal to a camera of the mobile device.

8. A tissue imaging system for visualizing of tissue health indicators, the system comprising: a portable computing device, an image capture unit, and an illumination unit, wherein: the illumination unit comprises one or more narrow band light sources configured to shine m flashes of light on a target area of the tissue at n predetermined wavelengths, wherein $n/4 \leq m \leq n$; and wherein m is a number of light flashes in one cycle and n is a number of wavelengths;
   the image capture unit and the illumination unit are configured to capture measurement data for the target area of the tissue; and
   the computing device comprises a processor configured to access and execute instructions in accordance with a tissue visualization application stored in a non-transitory computer-readable memory of the computing device, for capturing measurement data, and pre-processing and processing the measurement data to generate the tissue health indicators.

9. The tissue imaging system of claim 8, wherein the computing device comprises a mobile device and the image capture unit is a camera integrated with the mobile device.

10. The tissue imaging system according to claim 8, wherein the illumination unit comprises:

a portable housing for detachable attachment proximal to the image capturing unit.

11. The tissue imaging system according to claim 8, wherein the portable illumination unit further comprises a wireless communication module for receiving commands from the computing device.

12. A tissue visualization system operatively connected to one or more tissue imaging systems according to claim 8, comprising a communications module for communicating with the one or more tissue imaging systems, a system processor, and system non-transitory computer-readable memory thereon, configured to receive the measurement data and the tissue health indicators from the one or more tissue imaging systems and to generate a visualization of tissue health indicators of tissue images received from the one or more tissue imaging systems, for display to a user display unit.

13. A method for generating visualizations of tissue, the method comprising:
   positioning a computing device at a proper distance from a target area of the tissue for capturing an image of the target area, the computing device comprising a processor and a non-transitory computer-readable memory storing computer-executable instructions comprising a tissue visualization application;
   capturing measurement data using an image capturing unit and an illumination unit, the image capturing unit and the illumination unit communicatively coupled to the computing device and the illumination unit configured to shine m flashes of light on the target area of the tissue at n predetermined wavelengths during capturing of the measurement data, wherein n/4≤m≤n; and wherein m is a number of light flashes in one cycle and n is a number of wavelengths;
   pre-processing the measurement data using the tissue visualization application to obtain reflectance images;
   extracting indications of tissue health indicators from the pre-processed measurement data;
   generating interface elements corresponding to the visualization tissue health indicators; and
   at least one of storing or transmitting the extracted indications of the tissue health indicators.

14. The method of claim 13 further comprising, prior to capturing the measurement data, capturing a reference image, wherein the positioning the computing device for the reference image capturing comprises positioning the computing device using a reference object.

15. The method of claim 13, wherein the illumination unit and the computing device are configured to provide a working distance of 15±5 cm from the target area of tissue.

16. The method of claim 15, wherein the positioning of the computing device for capturing the measurement data comprises positioning the computing device using a self-reference object.

17. The method according to claim 13, wherein pre-processing comprises at least one of:
   (i) registering images to avoid camera motion artifacts,
   (ii) subtracting images with no illumination from the illumination unit from images with illumination from the illumination unit to account for a presence of ambient light,
   (iii) recalibrating each measurement accordingly to control parameters related to intensity of illumination using a self-reference object positioned within the target area,
   (iv) dividing the captured images on reference images to obtain reflectance images, or
   (v) flattening the reflectance images to account for reflections from curved surfaces.

18. The method according to claim 13, wherein exposure time of the image capturing unit is T and a flash time is said T or any multiple of said T.

19. The method according to claim 18, wherein the exposure time of the image capturing unit is 50 ms.

20. The method according to claim 13, wherein the measurement data comprises wound-related data.

\* \* \* \* \*

(12) POST-GRANT REVIEW CERTIFICATE (270th)

United States Patent
Saiko et al.

(10) Number: US 11,266,345 J1
(45) Certificate Issued: Jan. 24, 2024

(54) APPARATUS FOR VISUALIZATION OF TISSUE

(71) Applicants: Guennadi Saiko; Andrei Betlen; Kenneth Macko

(72) Inventors: Guennadi Saiko; Andrei Betlen; Kenneth Macko

(73) Assignee: SWIFT MEDICAL INC.

Trial Number:

PGR2022-00041 filed May 12, 2022

Post-Grant Review Certificate for:

Patent No.: 11,266,345
Issued: Mar. 8, 2022
Appl. No.: 17/260,664
Filed: Jan. 15, 2021

The results of PGR2022-00041 are reflected in this post-grant review certificate under 35 U.S.C. 328(b).

POST-GRANT REVIEW CERTIFICATE
U.S. Patent 11,266,345 J1
Trial No. PGR2022-00041
Certificate Issued Jan. 24, 2024

AS A RESULT OF THE POST-GRANT REVIEW PROCEEDING, IT HAS BEEN DETERMINED THAT:

Claims 1-20 are cancelled.

\* \* \* \* \*